(12) United States Patent
Moulton et al.

(10) Patent No.: US 12,220,383 B2
(45) Date of Patent: Feb. 11, 2025

(54) SECUREMENT ASSEMBLY FOR ENTERAL AND VESICAL ACCESS DEVICES AND RELATED METHODS

(71) Applicant: The Regents of The University of Colorado, County, CO (US)

(72) Inventors: Steven Lee Moulton, Denver, CO (US); Tyler Mironuck, Denver, CO (US); Brian J. Heckman, Fort Lauderdale, FL (US)

(73) Assignee: The Regents of The University of Colorado, Denver, CO (US)

( * ) Notice: Subject to any disclaimer, the term of this patent is extended or adjusted under 35 U.S.C. 154(b) by 739 days.

(21) Appl. No.: 17/297,726

(22) PCT Filed: Nov. 20, 2019

(86) PCT No.: PCT/US2019/062469
§ 371 (c)(1),
(2) Date: May 27, 2021

(87) PCT Pub. No.: WO2020/112461
PCT Pub. Date: Jun. 4, 2020

(65) Prior Publication Data
US 2022/0040046 A1  Feb. 10, 2022

Related U.S. Application Data

(60) Provisional application No. 62/771,963, filed on Nov. 27, 2018.

(51) Int. Cl.
*A61J 15/00* (2006.01)
(52) U.S. Cl.
CPC ....... *A61J 15/0057* (2013.01); *A61J 15/0015* (2013.01)

(58) Field of Classification Search
CPC ..... A61J 15/0057; A61J 15/0015; A61F 5/44; A61F 5/4408; A61M 25/02;
(Continued)

(56) References Cited

U.S. PATENT DOCUMENTS 2,765,949 A  10/1956  Hillman
3,086,676 A   4/1963  Dilatush
(Continued)

FOREIGN PATENT DOCUMENTS

CN  113660971 A  11/2021
EP   3886966 A1  10/2021
(Continued)

OTHER PUBLICATIONS

International Preliminary Report on Patentability, International Application No. PCT/US19/062469 mailed on Jun. 10, 2021, 14 pages.
(Continued)

*Primary Examiner* — Michael J Tsai
*Assistant Examiner* — Neeraja Gollamudi
(74) *Attorney, Agent, or Firm* — Capital Patent & Trademark Law Firm, PLLC

(57) ABSTRACT

The present disclosure provides a securement assembly for an enteral access device or vesical access device ("access device"). The securement assembly includes a base and a lid. The base is generally configured to support an external port of the access device and the lid is pivotably coupled to the base. The base comprises a border rim and a central portion, wherein the border rim is configured to engage a skin surface of a patient around a stoma and the central portion is configured to engage the external port of the access device. The central portion may comprise opposing side arms defining an aperture through which a tube of the access device extends.

23 Claims, 20 Drawing Sheets

(58) Field of Classification Search
CPC .. A61M 2025/0246; A61M 2025/0266; A61M 2025/0273; A61M 2025/028; B65D 47/0885; B65D 47/0895; B65D 2251/1008

See application file for complete search history.

(56) References Cited

U.S. PATENT DOCUMENTS

| | | | |
|---|---|---|---|
| 3,834,380 A * | 9/1974 | Boyd | A61M 25/02 128/DIG. 26 |
| 4,473,168 A | 8/1984 | Cox | |
| 4,634,421 A | 1/1987 | Hegemann | |
| 5,346,099 A * | 9/1994 | Salmon | B65D 47/0861 220/840 |
| 5,562,107 A | 10/1996 | Lavender et al. | |
| 6,071,268 A | 6/2000 | Wagner | |
| 6,231,549 B1 | 5/2001 | Noecker et al. | |
| 6,482,183 B1 * | 11/2002 | Pausch | A61J 15/0015 604/174 |
| 6,765,122 B1 | 7/2004 | Stout | |
| 7,087,041 B2 | 8/2006 | vonDyck et al. | |
| 7,699,824 B2 | 4/2010 | Axelsson et al. | |
| 7,704,260 B2 | 4/2010 | Skakoon et al. | |
| 7,732,036 B2 * | 6/2010 | Etchells | B65D 81/264 604/385.01 |
| 8,545,469 B2 | 10/2013 | Anderson et al. | |
| 8,979,812 B2 | 3/2015 | Loecher | |
| 9,132,039 B2 | 9/2015 | Clifford et al. | |
| D789,527 S | 6/2017 | Kyvik | |
| 2003/0032932 A1 | 2/2003 | Stout | |
| 2004/0106908 A1 | 6/2004 | Leise et al. | |
| 2005/0033240 A1 | 2/2005 | Oishi et al. | |
| 2006/0084923 A1 | 4/2006 | Lotartaro | |
| 2006/0224131 A1 | 10/2006 | Calvert | |
| 2007/0265572 A1 * | 11/2007 | Smith | A61M 25/02 604/174 |
| 2008/0009779 A1 | 1/2008 | Fabo et al. | |
| 2010/0022961 A1 | 1/2010 | Dewey | |
| 2010/0057013 A1 | 3/2010 | Harada | |
| 2010/0331785 A1 | 12/2010 | Fabo et al. | |
| 2011/0137271 A1 | 6/2011 | Andresen et al. | |
| 2012/0197202 A1 * | 8/2012 | Wright | A61M 25/02 604/174 |
| 2012/0259301 A1 | 10/2012 | Polnik et al. | |
| 2012/0271240 A1 * | 10/2012 | Andino | A61M 25/02 604/180 |
| 2012/0302981 A1 | 11/2012 | Lam | |
| 2014/0046238 A1 * | 2/2014 | Leibowitz | A61F 13/00063 602/48 |
| 2015/0335874 A1 | 11/2015 | Phillips et al. | |
| 2017/0326340 A1 * | 11/2017 | Howell | A61M 25/02 |
| 2020/0146944 A1 | 5/2020 | Moulton et al. | |

FOREIGN PATENT DOCUMENTS

| | | | |
|---|---|---|---|
| JP | 58-137773 | 9/1983 | |
| JP | U S60-47241 A | 4/1985 | |
| JP | 2000-157636 A | 6/2000 | |
| JP | 2001-522664 | 8/2000 | |
| KR | 101887435 B1 * | 8/2018 | A61M 1/00 |
| WO | WO-2018-200721 A1 | 11/2018 | |
| WO | WO 2020-112461 A1 | 6/2020 | |

OTHER PUBLICATIONS

Extended European Search Report, European Application No. 19889090.7 dated Jul. 13, 2022, 8 pages.
Office Action, Japanese Application No. 2021-530067, date Aug. 5, 2022, 7 pages.
Office Action, Canadian Application No. 3,121,115, dated Sep. 8, 2022, 3 pages.
International Search Report and Written Opinion for International Application No. PCT/US2018/029434 mailed on Jul. 23, 2018, 37 pages.
International Preliminary Report on Patentability, International Application No. PCT/US2018/029434 mailed on Oct. 29, 2019, 7 pages.
Communication pursuant to Rules 161(2) and 162 EPC for International Application No. PCT/US2018/029434, dated Dec. 3, 2019, 3 pages.
International Search Report and Written Opinion for International Application No. PCT/US2019/062469 mailed on Jan. 15, 2020, 20 pages.
Extended European Search Report, International Application No. PCT/US2018/029434 dated Nov. 30, 2020,.
Communication pursuant to Rules 70(2) and 70a(2) EPC for International Application No. PCT/US2018/029434, dated Dec. 20, 2020, 1 page.
Notice of Allowance, Japanese Application No. 2021-530067, date Nov. 18, 2022, 3 pages.
Office Action, Chinese Application No. 201980090525.X, dated Dec. 13, 2022, 15 pages.

* cited by examiner

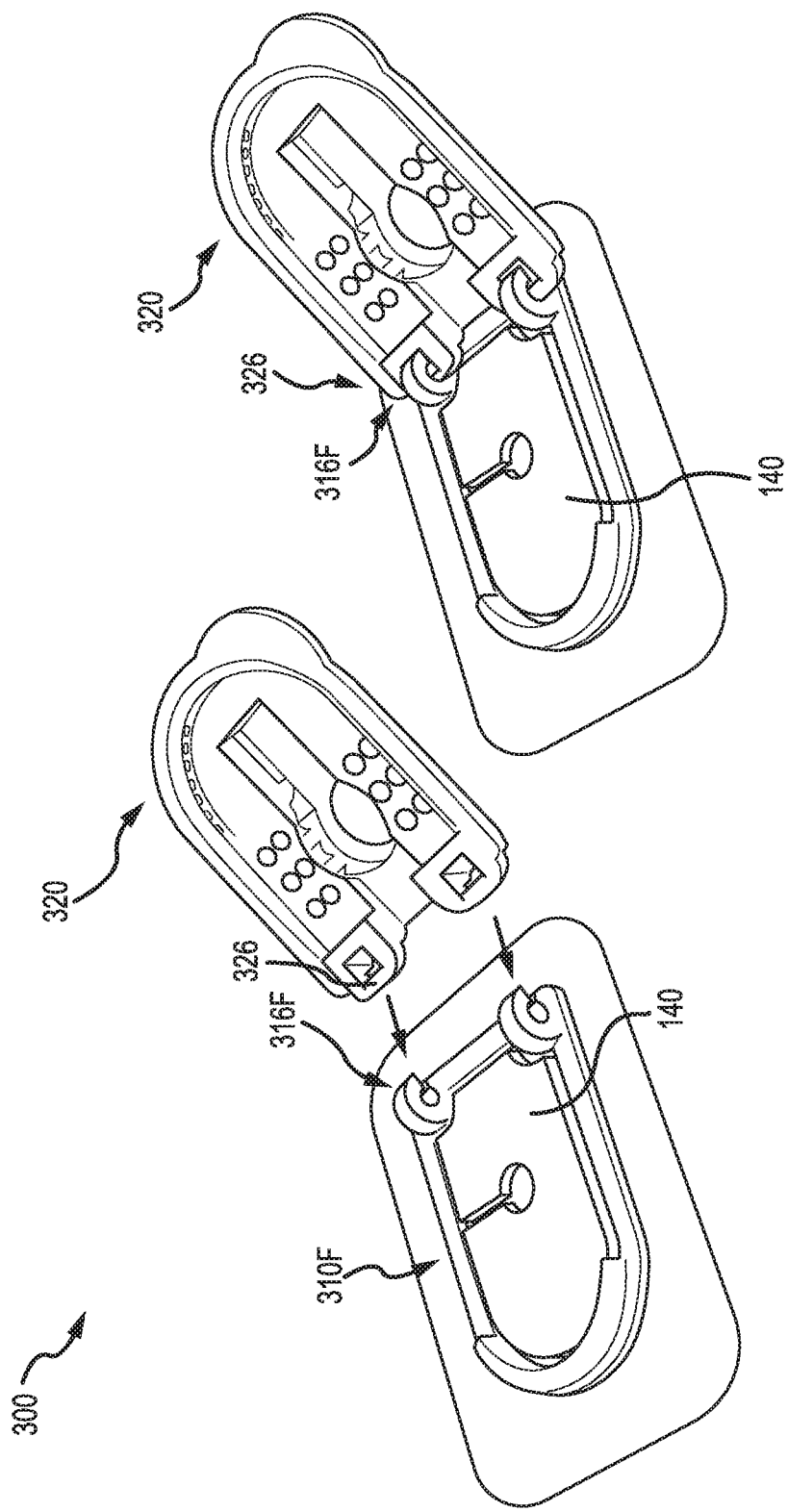

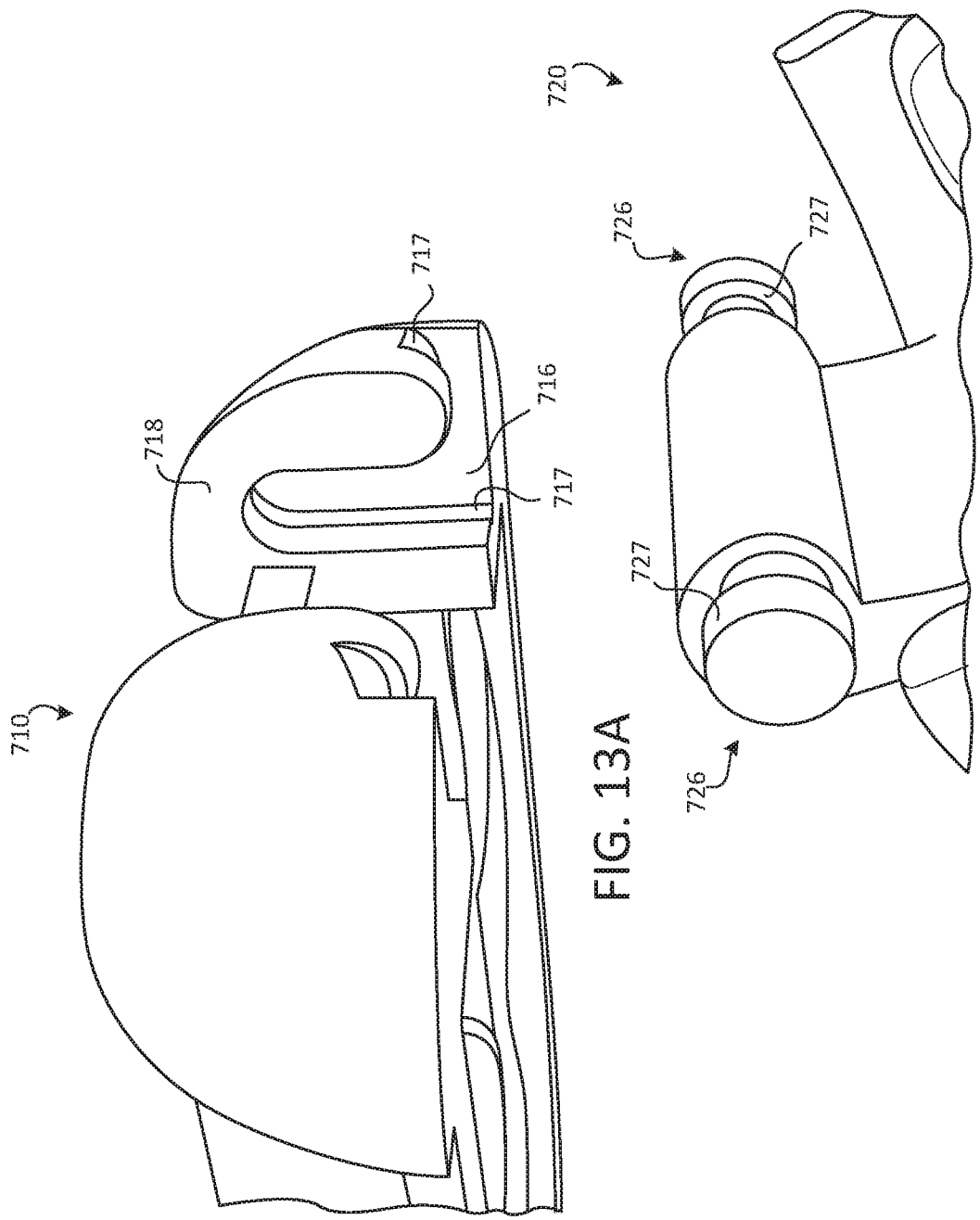

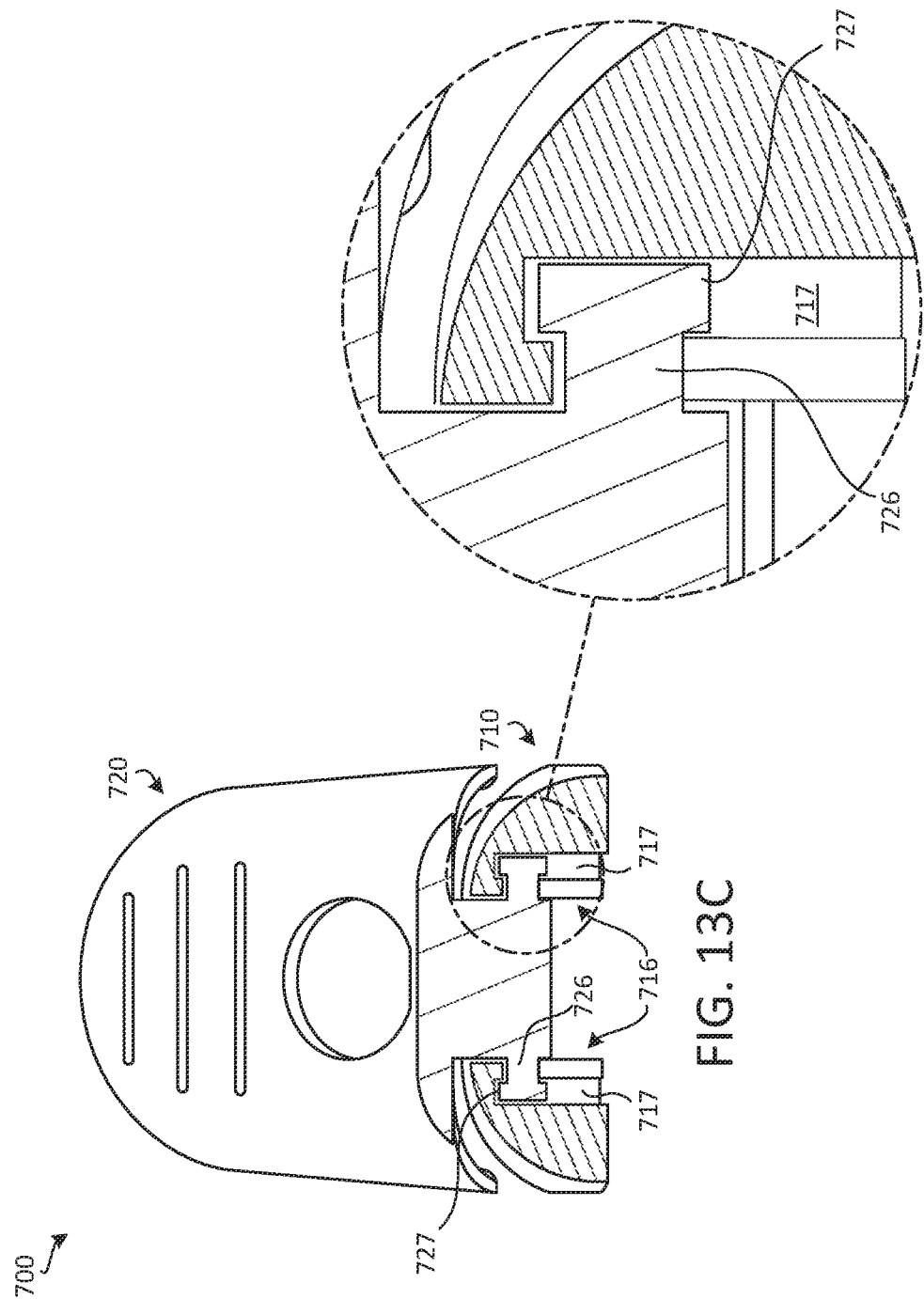

SECUREMENT ASSEMBLY FOR ENTERAL AND VESICAL ACCESS DEVICES AND RELATED METHODS

CROSS-REFERENCE TO RELATED APPLICATIONS

This application is a 35 U.S.C. § 371 national phase application of PCT/US19/062469 (WO-2020-112461-A1), filed on Nov. 20, 2019, entitled "Securement Assembly for Enteral and Vesical Access Devices and Related Methods", which application claims priority to U.S. provisional patent application Ser. No. 62/771,963, filed on Nov. 27, 2018, the entire contents of both are incorporated herein by reference in its entirety.

FIELD

The present disclosure relates to securement and stabilization of enteral and vesical access devices, and more specifically to a securement assembly, and related methods, for securing and stabilizing enteral and vesical access devices.

BACKGROUND

Certain individuals require feeding assistance due to swallowing disorders, issues gaining weight, poor hydration, or congenital anomalies within their digestive system. Others may require intermittent or continuous access to the urinary bladder for irrigation, decompression or drainage. For example, conventional access devices may be referred to by the following names gastrostomy tube (g-tube), gastrostomy button (g-button), gastrojejunostomy button (gj-button), jejunostomy device or button (j-button), cecostomy button or tube, enteral access device (EAD), or vesicostomy button, among others (generally "access devices"). These access devices generally allow food, fluids, nutritional supplements, and medications to be delivered directly into the stomach, small or large bowel of a patient, or the bladder. In other settings, such as anorectal anomalies or chronic constipation, these access devices may be inserted into the cecum (proximal colon) to enable antegrade enemas. In still other settings these access devices may be used for gastric, intestinal or bladder decompression. Regardless of their location in the intestinal tract, these access devices are generally used at a minimum for several months, but in some cases are required for years or a patient's entire life.

Even though the placement of an access device, such as an enteral access device, is a straightforward procedure, there are several bothersome postoperative complications that may arise. Most common are the formation of granulation tissue and leakage of gastric, intestinal or urinary contents around the access device. These issues generally arise from a lack of securement between the access device and the patient. In other words, the tube of the access device is generally free to rotate and move both laterally and vertically within the stoma. This movement exposes the button (i.e., the external port or portion of the access device) to external forces (clothes catching, accidental hand swipe, etc.) and human-related forces (twisting of the abdomen, skin folding, coughing, etc.), which can cause friction within the lumen of the stoma and on the surface of the skin. These forces can similarly lead to compression of the internal retention balloon of the access device against the inner wall of the stomach, and shearing between the access device and the patient's skin, which may widen the stoma.

One conventional securement technique that doctors and nurses recommend is a "tic-tac-toe" taping method. This involves sliding a 2×2-inch gauze pad between the hub of the device and the patient's skin, in order to absorb leakage from the stomach, intestine, bladder or the tract itself. The dressing is then taped around the perimeter of the tube's entry hole to form a tic-tac-toe grid using tape (e.g., hypoallergenic tape). Unfortunately, this method has not proven to be reliable or effective in stabilizing these access devices, and has various other shortcomings.

SUMMARY

In various embodiments, the present disclosure provides a securement assembly for an enteral access device or vesical access device ("access device"). The securement assembly includes a base and a lid, according to various embodiments. The base may be configured to support an external port of the access device and the lid may be pivotably coupled to the base.

In various embodiments, the base comprises a border rim and a central portion, wherein the border rim is configured to engage a skin surface of a patient around a stoma and the central portion is configured to engage the external port of the access device. In various embodiments, the central portion comprises opposing side arms defining an aperture through which a tube of the access device extends. In various embodiments, the side arms of the central portion are resiliently flexible to facilitate selective enhanced retention of the external port of the access device. In various embodiments, an underside of the lid comprises engagement features configured to engage the side arms of the central portion to transfer a user applied compression force from the lid to the central portion to facilitate the selective enhanced retention of the external port of the access device and to stabilize the enteral or vesical access device during attachment of an extension tube.

In various embodiments, the lid defines slits to facilitate deformation of the lid in response to the user applied compression force. The central portion is a cantilevered extension from a rear of the base, according to various embodiments. The securement assembly may further include an absorbent member defining a central aperture and a slit. The absorbent member may be configured to be slid under the cantilevered extension and over the border rim into engagement with the skin surface around the stoma in an annular space defined between the border rim and the tube of the access device, with the tube of the access device extending through the central aperture. In various embodiments, the absorbent member has opposing wings configured to extend beyond lateral sides of the base. At least one of the border rim and a border edge of the lid at the lateral sides of the base may define a notch to accommodate the opposing wings of the absorbent member.

In various embodiments, the border rim at a rear of the base defines a gap through which a connecting strap of a cap of the access device is configured to extend. In such embodiments, the lid is pivotably coupled to the base at a hinge axis, wherein the gap defined by the border rim of the base is configured such that the connecting strap of the access device either intersects the hinge axis or extends below the hinge axis.

In various embodiments, the lid is selectively detachably coupled to the base. In response to the lid being in a first angular orientation relative to the base, the lid is prevented from being decoupled from the base (i.e., is in a "child proof state"), wherein in response to the lid being in a second angular orientation relative to the base, the lid is detachable from the base. In various embodiments, the lid is configured to be coupled to the base before the base is adhered to a skin surface of a patient such that the securement assembly is in the child proof state in response to the lid being coupled to the base and the base being adhered to the skin surface.

In various embodiments, a rear of the base comprises a curved prong and the lid comprises a rod, wherein a hinge axis is formed between the base and the lid in response to the curved prong receiving the rod. In various embodiments, lateral sides of a rear of the base define opposing channels that face inward, wherein the lid comprises laterally extending cylindrical protrusions, wherein a hinge axis is formed between the base and the lid in response to the opposing channels receiving the laterally extending cylindrical protrusions. In various embodiments, wherein each channel of the opposing channels has an open lower end and a closed upper end. The closed upper end of each channel may define a dimple configured to receive an end of a respective cylindrical protrusion of the laterally extending cylindrical protrusions. The opposing channels may include tapering walls that converge toward each other from the open lower end to the closed upper end.

In various embodiments, the laterally extending cylindrical protrusions are opposing ends of a continuous section of material of the lid that extends between the opposing ends. The opposing channels may define tracks and the laterally extending cylindrical protrusions may comprise flange portions configured to be respectively received within the tracks. In various embodiments, the tracks comprise rounded entry corners to facilitate insertion of the flange portions within the tracks. In various embodiments, at least a rear portion of a border edge of the lid comprises a chamfer. In various embodiments, engagement of the rear portion of the border edge of the lid with a rear of the base facilitates maintaining the securement assembly in the child proof state.

In various embodiments, the lid defines a receptacle for detachably retaining a cap of the access device. The securement assembly may also further include a deformable lid cover configured to be detachably coupled to the lid to cover an upper surface of the lid. In various embodiments, tangents of outer surfaces of the base and the lid adjacent junction interfaces between the base and the lid are substantially parallel, thus preventing articles from being snagged at the junction interfaces between the base and the lid.

Also disclosed herein, according to various embodiments, is a securement assembly for an enteral access device or vesical access device ("access device"). The securement assembly may include a base comprising a border rim and a central portion. The border rim is configured to engage a skin surface of a patient around a stoma and the central portion is configured to engage an external port of the access device. The securement assembly may further include a lid selectively detachably and pivotably coupled to the base.

Also disclosed herein, according to various embodiments, is a method of installing a securement assembly for an enteral access device or vesical access device ("access device"). The method may include coupling a lid of the securement assembly to a base of the securement assembly. The method may further include, after coupling the lid of the securement assembly to the base of the securement assembly, coupling a border rim of the base to a skin surface of a patient about a stoma of the patient; and supporting an external port of the access device by a central portion of the base.

The forgoing features and elements may be combined in various combinations without exclusivity, unless expressly indicated herein otherwise. These features and elements as well as the operation of the disclosed embodiments will become more apparent in the following description and accompanying drawings.

BRIEF DESCRIPTION OF THE DRAWINGS

FIGS. 9A, 9B, 9C, 9D, 9E, 9F, 9G, and 9H are views of portions of a securement assembly showing various features that facilitate a hinged connection between a base and a lid of the securement assembly, in accordance with various embodiments;

FIGS. 13A, 13B, 13C, and 13D are views of another hinged connection configuration between a base and a lid of a securement assembly, in accordance with various embodiments;

Figure 1A:
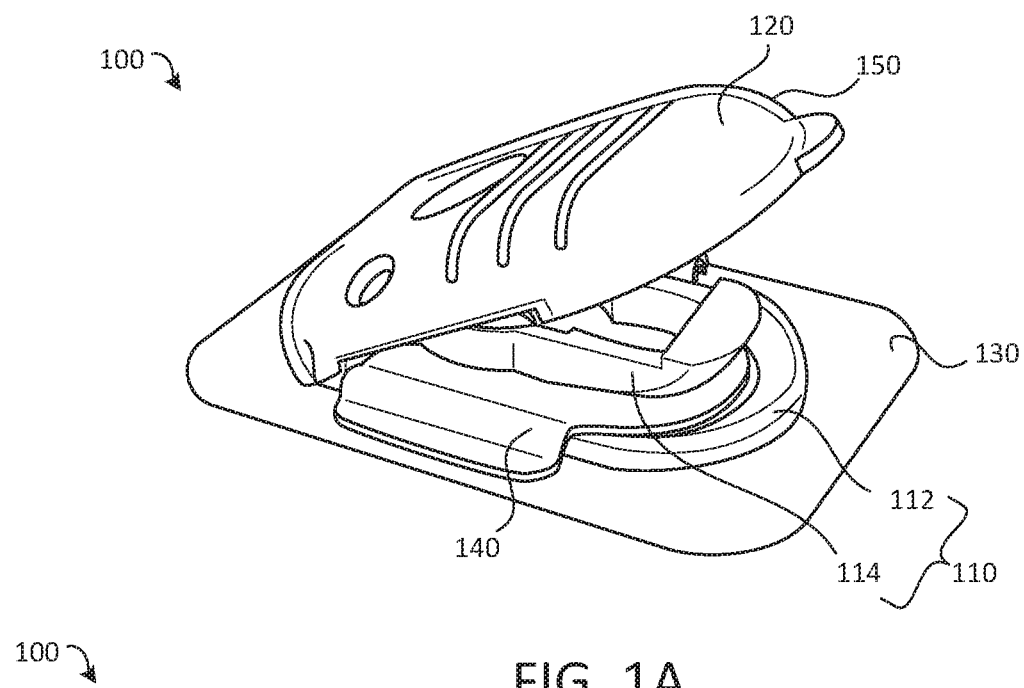
FIGS. 1A and 1B are perspective views of a securement assembly, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered with the drawing figures.

DETAILED DESCRIPTION

The detailed description of exemplary embodiments herein refers to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

In accordance with example embodiments, the present disclosure provides a securement assembly for supporting and stabilizing an enteral access device or a vesical access device (generally an "access device"). As used herein the term "access device" refers to a device to provide access through a gastrostomy, a jejunostomy, a cecostomy, or a vesicostomy, among others. The access device may include a tube, one or more retention features, and a button interface for engaging with feeding tubes and other components, as described in greater detail below. The securement assembly disclosed herein is generally configured to support, secure, retain, and/or protect the access device, thereby mitigating the formation of granulation tissue and/or inhibiting leakage of gastric, intestinal or bladder contents about the access device, according to various embodiments.

The securement assembly may also facilitate quick and easy engagement/connection between the access device and extension feeding or drainage tubes and other such components, and may also be shaped and configured to prevent objects or articles from catching on the securement assembly. Further, it will be apparent to those skilled in the art that various modifications and variations can be made in the present disclosure without departing from the spirit or scope of the disclosure. For example, though many details and embodiments disclosed herein pertain to using the securement assembly as a dressing for a gastrostomy button, the disclosure is not so limited. That is, the details and embodiments of the securement assembly disclosed herein may be applied more generally to dressings for other enteral, vesical, and/or parenteral access devices. Thus, it is intended that the embodiments described herein cover the modifications and variations of this disclosure provided they come within the scope of the appended claims and their equivalents.

Figure 1B:
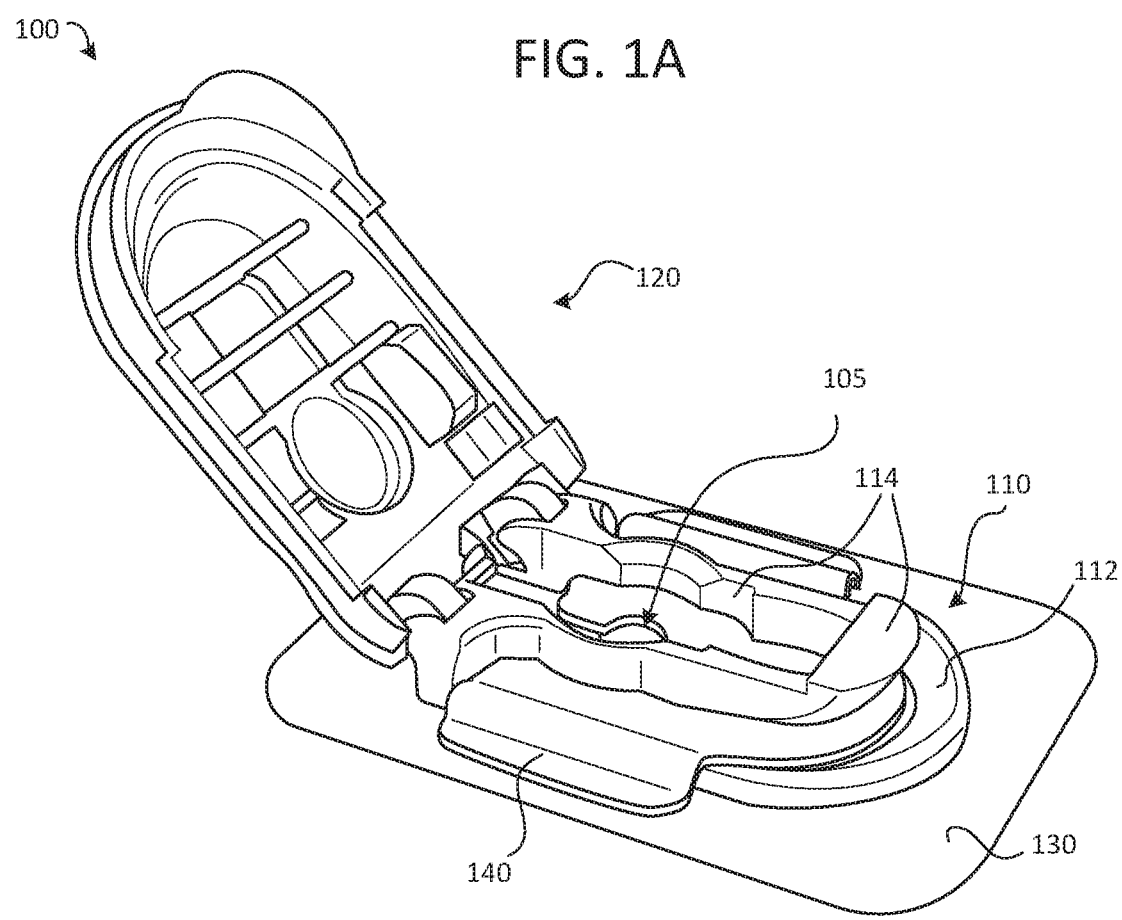
Figure 2:
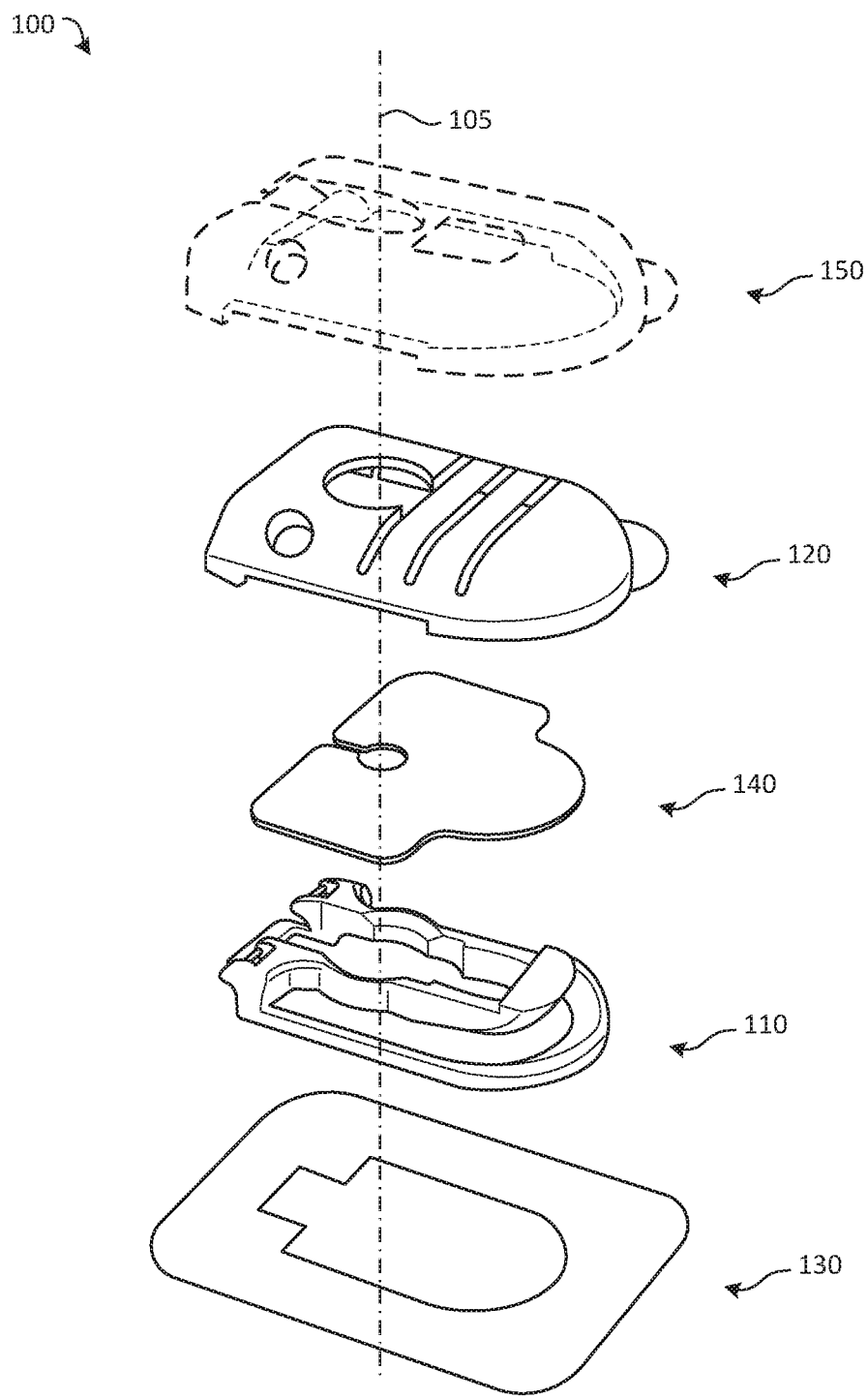
FIG. 2 is an exploded perspective view of a securement assembly, in accordance with various embodiments.

In various embodiments, and with reference to FIGS. 1A, 1B, and 2, the securement assembly 100 comprises a base 110 and a lid 120. The base 110 is generally configured to support an external port of an access device and the lid 120 is pivotably coupled to the base 110, according to various embodiments. That is, the securement assembly 100 is generally configured to be adhered to a skin surface of a patient around a stoma to stabilize, support, secure, and otherwise retain an access device extending through the stoma. The securement assembly 100 may also comprise an adhesive layer 130, an absorbent member 140, and a lid cover 150. The lid cover 150 may facilitate covering the lid 120 to prevent objects or articles from being snagged on the device, but in various embodiments the lid 120 is configured to be substantially smooth/continuous enough that no lid cover 150 is warranted. The adhesive layer 130 may be coupled to (or integrated with) the base 110 and may enable adhesive attachment of the securement assembly 100 to the patient, the absorbent member 140 may be generally configured to fit around the tube/stem of the access device to absorb any fluid leakage, and the lid cover 150 may extend across an outer surface of the lid 120 to create a substantially smooth, catch-free outer surface to inhibit articles or objects from being caught on the assembly and exerting a force on the access device. The base 110, the lid 120, the adhesive layer 130, the absorbent member 140, and the lid cover 150 are described in more detail in the following pages.

The securement assembly 100 may facilitate securement by absorbing and/or dispersing forces applied to the access device. For example, the 'forces' that can be dispersed may be external forces (clothes catching, accidental hand swipe, etc.) and/or human-related forces (twisting of the abdomen, skin folding, coughing, etc.). The base 110 and the adhesive layer 130 may be integrated together as a single unit. The adhesive layer 130 may also facilitate absorbing and/or dispersing the forces applied to the access device.

In various embodiments, the lid 120 functions as a physical barrier/shield to prevent articles or objects contacting the port of the access device. The lid 120 may also define, together with the base 110 and the skin surface of the patient, a volume/space for the absorbent member 140 to be housed. Thus, the lid 120 may facilitate retention of the absorbent member 140 within this volume/space, thereby helping the absorbent member 140 stay in a desired position relative to the access device and stoma. In various embodiments, the lid 120 is detachable and/or pivotable relative to the base 110, thereby enabling a practitioner access to the retained absorbent member 140 to replace the absorbent member 140 and/or inspect the stoma and stem/port of the access device.

In various embodiments, the base 110 includes a border rim 112 configured to engage the skin surface of the patient around the access device. The base 110 may also include a central portion 114 configured to engage the external port of the access device. The base 110 may provide one, two, or three-dimensional stability by limiting displacement of the access device in one or more directions. For example, the central portion 114 of the base 110 that directly engages and supports the external port of the access device may be a cantilevered extension from border rim 112, as described in greater detail below. The central portion 114 may be elevated relative to the border rim 112, thus allowing the absorbent member 140 to be retained between the border rim 112 and the central portion 114. Additional details pertaining to the border rim 112 and the central portion 114 are included below.

As used herein, the terms "upper," "above," "elevated," and/or "top" refer to components or surfaces that are facing away from or are disposed comparatively further away from the skin surface of the patient. Similarly, the terms "lower,"

"below," under," and/or "bottom" refer to components or surfaces that are facing toward or are disposed comparatively closer to the skin surface of the patient. Further, the terms "inner" and "outer" refer to positions relative to the stoma axis 105. That is, the access device extending through the stoma may be generally referred to as a center of the assembly, and thus components or surfaces that are described as "inner" face toward or are disposed comparatively closer to the stoma axis 105 and components or surfaces that are described as "outer" face away from or are disposed comparatively further from the stoma axis 105.

In various embodiments, the lid 120 may be selectively detachably coupled to the base 110. That is, the lid 120 may be disconnected from the base 110, thus allowing the base 110 to be swapped/replaced with a new one while allowing the practitioner to reuse the lid 120 with the replacement base 110. For example, the base 110 and the adhesive layer 130 may be configured to adhere to the skin surface of the patient for a period of several days (e.g., 7-10 days), during which time the absorbent member 140 may be replaced multiple times. After the period of several days (e.g., in response to degradation of the adhesive), the adhesive layer 130 and base 110 may be removed from the skin surface, the lid detached from the base 110, and a new base installed with the existing lid 120, according to various embodiments. Accordingly, the securement assembly helps practitioners and patients avoid daily application/re-application of tape and gauze to secure the access device, thereby reducing adhesive trauma to the skin around the gastrostomy.

Returning to the concept of the lid 120 being pivotable relative to the base 110, the hinged connection may be disposed at a rear of the securement assembly 100, and a front/leading edge of the securement assembly 100 may comprises a snap-fit retention configuration between the base 110 and the lid 120. The lid 120 may further include a grasping tab to allow the practitioner to reverse the snap-fit retention to decouple the front/leading edge of the securement assembly to allow the lid 120 to pivot about its hinged connection relative to the base 110. Additional details pertaining to the detachable and pivoting coupling mechanisms, as well as details pertaining to a method of installing the securement assembly, are included below.

The adherence provided by the adhesive layer 130 may be temporary (e.g., minutes, hours, or days) or semi-permanent (e.g., days, weeks, or months). In various embodiments, the adhesive layer 130 may be easily and atraumatically removable, so as to not cause pain or a significant rash or other irritation to the patient upon removal. Tape may be used in place of the adhesive layer to affix the base 110 to the skin surface of the patient. The outer perimeter of the adhesive layer 130 can be elliptical (e.g., circular ovoid, obround, or the like) or polygonal (e.g., non-elliptical, such as triangular, rectangular, square, hexagonal, or the like). Alternatively, the perimeter of the adhesive layer 130 may be specific to an end-use (e.g., may be customized by stamping, knife CNC, waterjet, laser, or manual alteration). In example embodiments, adhesive layer 130 is flexible so as to conform to a skin surface or other site where an enteral or vesical access device is prescribed. The adhesive layer may be comprised of a fabric or polymeric film with an adhesive bottom. Suitable materials for the adhesive layer 130 include, but are not limited to silicone or silicone-free adhesives with nonwoven, woven, acrylic, or polyurethane backings that are biocompatible. In various embodiments, the upper surface of adhesive layer 130 does not comprise any backing, but rather, comprises an adhesive (e.g., acrylic) to attach to the base 110.

Figure 3A:
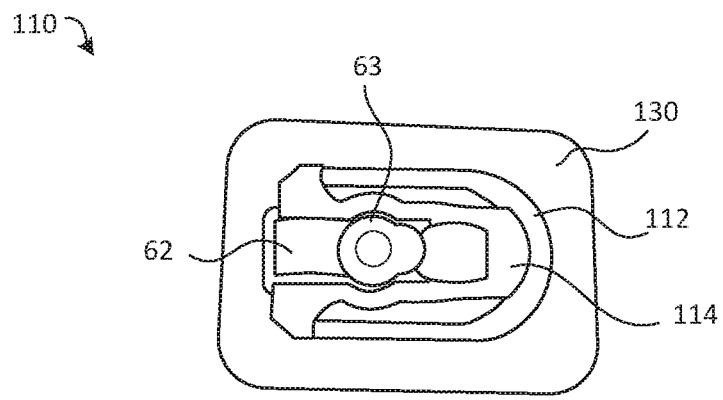
FIG. 3A is a top view of a securement assembly, in accordance with various embodiments.
Figure 3B:
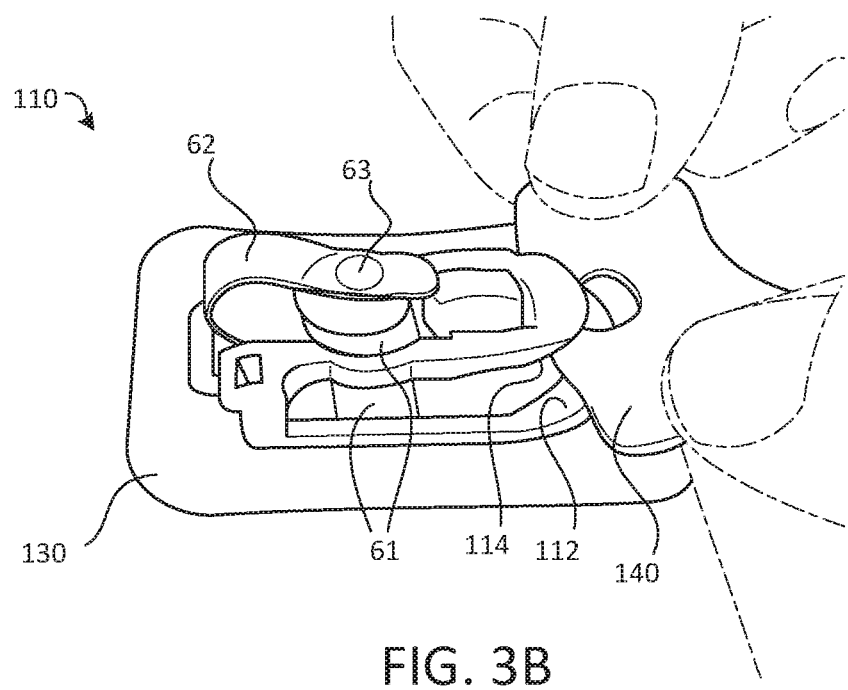
FIG. 3B is a perspective view of an absorbent member being installed to the securement assembly, in accordance with various embodiments.

In various embodiments, and with reference to FIGS. 3A and 3B, portions of an access device are shown relative to the base 110 of the securement assembly 100. The access device generally includes an external port 61, a connecting strap 62, and a cap 63. The cap 63 may be detachably engaged with the external port 61 to close off the channel through the stoma when transport through the access device is not required. The external port 61 may be referred to herein as a hub of the access device, and may be an enlarged portion, relative to the stem/tube passing through the stoma that is configured to engage the central portion 114 of the base 110 (as described in greater detail below). The external port 61, the connecting strap 62, and the cap 63 may be collectively referred to as the external components of the access device, or more generally the "button." The access device may be an AMT MiniONE® Button (Applied Medical Technology, Inc., Brecksville, OH) or MIC-KEY* Low-Profile enteral access device (Halyard Health, Alpharetta, Georgia), or similar low-profile enteral access device made by other manufacturers.

As mentioned above, and with reference to FIGS. 3A, 3B, 6A, and 6B, the central portion 114 of the base 110 may be an elevated and cantilevered extension from a rear of the border rim 112 of the base 110. The central portion 114 may comprise side arms 115 that are configured to support and engage the external port 61 of the access device. The absorbent member 140 may define a slit and a central aperture (i.e., a keyhole slit), and the absorbent member 140 be positioned into engagement around the stem of the access device by sliding the absorbent member 140 underneath the cantilevered and elevated central portion 114 of the base 110 but across the top surface of the border rim 112 of the base 110. Said differently, the stem/tube of the access device (below the external port 61) may be disposed within the keyhole slit of the absorbent member 140 once the absorbent member 140 is installed in a substantially annular space defined between the border rim 112 and the access device.

In various embodiments, the border rim 112 of the base 110 comprises a chamfer to facilitate insertion, and subsequent extraction after use, of the absorbent member 140 relative to the annular volume. Correspondingly, the front lower surface of the cantilevered extension of the central portion 114 may have a similar chamfer/taper to facilitate insertion and extraction of the absorbent member 140 underneath the elevated central portion 114 (see FIG. 3B). In various embodiments, the lid of the securement assembly may include one or more features configured to engage/pierce the absorbent member 140 upon closing the lid, thereby facilitating subsequent extraction of the absorbent member 140 by the opening action of the lid. In various embodiments, the securement assembly 100 may include a wrap configured to extend around a forward side of the cap 63 of the access device and/or a forward side of the central portion of the base to facilitate insertion and extraction of the adhesive member 140. That is, the securement assembly may further include a strap, wrap, or other capping feature that is configured to extend around a forward side of components of the access device and/or a forward side of the base 110 to consolidate and/or compact these components in order to facilitate insertion of the absorbent member 140 (i.e., prevent the absorbent member from catching on forward side protrusions or edges of the assembly/access device).

In various embodiments, and with momentary reference to FIGS. 1A and 1B, the absorbent member 140 may have one or more wings that are configured to extend beyond lateral sides of the base 110. That is, portions (e.g., wings)

of the absorbent member 140 may extend beyond the footprint/perimeter of the base 110 and the lid 120, and these wings may be graspable by a practitioner to facilitate extraction of a spent absorbent member 140. In various embodiments, at least one of the border rim 112 of the base 110 and a border edge of the lid 120 along the lateral sides of the securement assembly defines a notch to accommodate the one or more wings of the absorbent member 140.

In various embodiments, the base 110 is coupled to (or integrated with) the adhesive layer 130. The outer perimeter of the base 110 may be smaller than the outer perimeter of adhesive layer 130. Similar to the aforementioned adhesive layer 130, the shape and size of the base 110 may be specific for a specific use or to a specific age group of patients. The base 110 may be rigid or semi-rigid. The base 110 may be made from plastic, composite, or polymeric materials. For example, the base 110 may include acrylonitrile butadiene styrene (ABS), nylon, a co-polymer, thermoplastic or other polymer, polycarbonate, or the like. In various embodiments, and as described in greater detail below, sections and/or portions of the base 110 may be resiliently flexible and may be made from other materials that are biodegradable.

In various embodiments, the base 110 generally surrounds and circumscribes the stoma axis 105. Accordingly, the base 110 may define an aperture that is coaxial with the stoma axis 105. Corresponding apertures may be defined in each of the adhesive layer 130, the absorbent member 140, the lid 120, and the lid cover 150.

In various embodiments, the absorbent member 140 is configured to absorb blood, plasma and/or gastric, intestinal or bladder exudates, and thereby reduce skin irritation. By minimizing the presence of these biological irritants, the absorbent member 140 may promote cleanliness at a stoma and may reduce stoma-related complications at the site where an enteral access device is prescribed. The outer perimeter of the absorbent member 140 may be configured to substantially fit within the border rim 112 of the base 110, or the absorbent member 140 may have wings/extension that extend beyond the base, as described above. Like the adhesive layer 130, the outer perimeter of absorbent member 140 can be elliptical, non-elliptical or random (e.g., cut by stamping, knife CNC, waterjet or laser). Also like adhesive layer 130, the absorbent member 140 may be flexible so as to conform to a stoma or other site where an enteral access device is prescribed.

In various embodiments, the absorbent member 140 is at least partially in contact with a stoma and a surrounding skin surface of the patient. In various embodiments, the absorbent member 140 is in total contact with the stoma and the surrounding skin surface. In this regard, the absorbent member 140 and the adhesive layer 130 are both in contact with a skin surface at the same time, according to various embodiments. Suitable materials for the absorbent member 140 include, but are not limited to, cotton gauze or other natural or man-made absorbent or wicking material that is one or more of hydroconductive, non-adherent, anti-bacterial, anti-fungal and biocompatible. Absorbent member can have a thickness of from about 0.5 to about 6 mm or more preferably, from about 1 to about 3 mm.

Figure 4B:
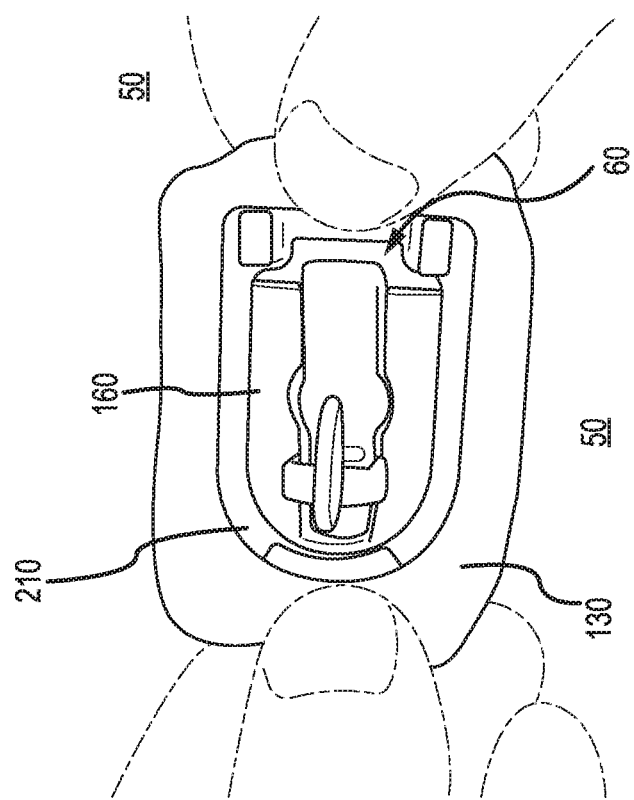
FIGS. 4A and 4B are top views of a spacer utilized to facilitate installation of a securement assembly around an external port of an access device, in accordance with various embodiments.
Figure 4A:
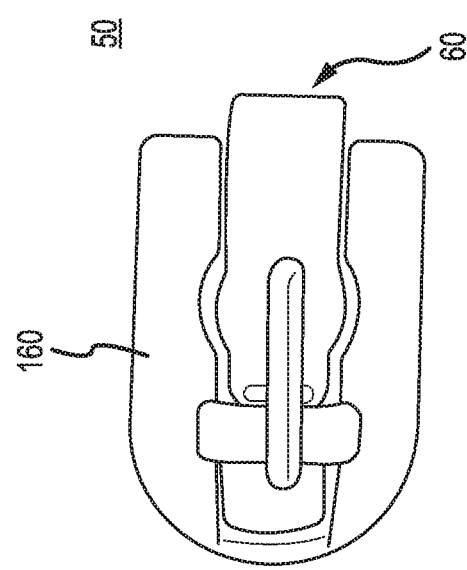

In various embodiments, and with reference to FIGS. 4A and 4B, the securement assembly may include a spacer 160 utilized to facilitate installation of the securement assembly around the external port of the access device. Though the aforementioned central portion 114 of the base 110 may function as a spacer and as a retention feature of the base 110, in certain embodiments the base 210 does not include the central portion. That is, the base 210 may include a rigid frame defining a border, with no centrally extending features. In such embodiments, in order to ensure the base 210 is properly positioned relative to the access device 60 during installation of the securement assembly, the spacer 160 may be positioned around the external port of the access device 60 and may be engaged against the skin surface 50 of the patient. The spacer 160 is configured, in various example embodiments to fit around the external port of the access device 60 and to extend in three or more locations to, or nearly to, the inside edges of the base 210, thus facilitating proper alignment of the base around the spacer 160. With the spacer 160 in position, the base 210 may then be installed around the spacer 160 (with accompanying adhesive layer 130), thus ensuring the proper spacing between the access device 60 and the border of the base 210. Once the base 210 is adhered to the skin surface 50, the spacer 160 may be removed to make room for insertion of an absorbent member.

Figure 5A:
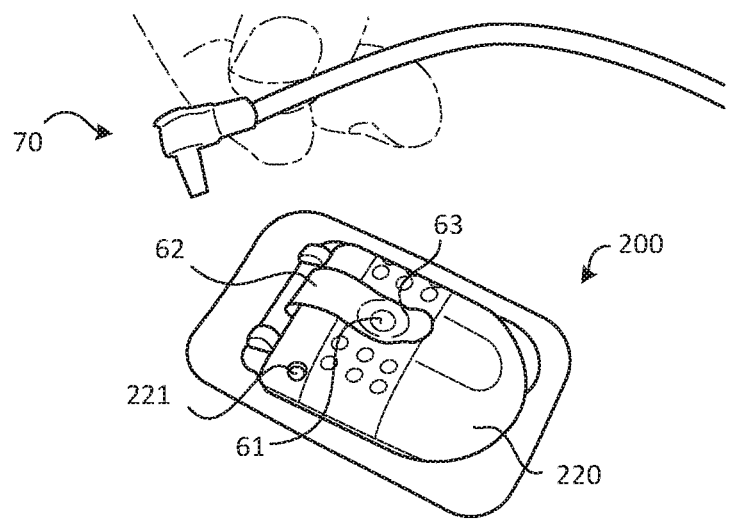
FIGS. 5A, 5B, and 5C are perspective views of a feeding tube being connected to an external port of an access device that is supported by a securement assembly, in accordance with various embodiments.
Figure 5B:
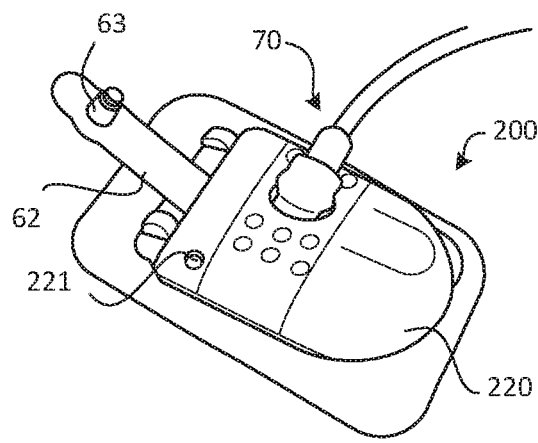
Figure 5C:
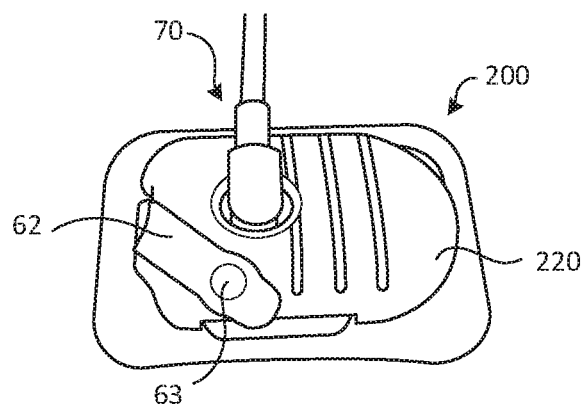
Figure 6A:
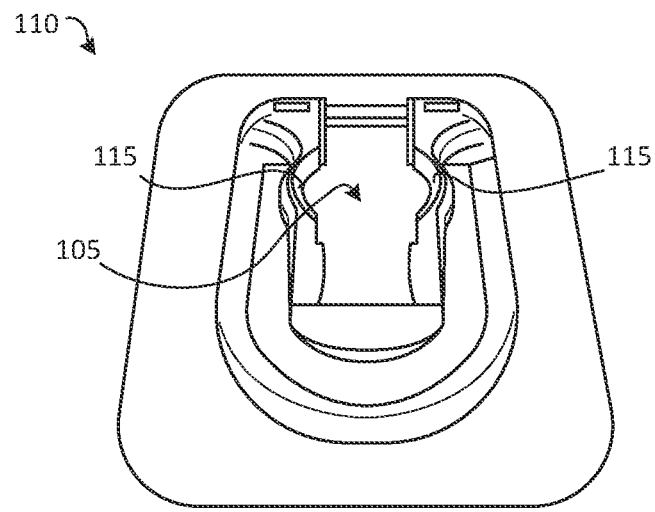
FIGS. 6A and 6B are perspective views of a securement assembly with features that facilitate selective enhanced retention of an external port of an access device, in accordance with various embodiments.
Figure 6B:
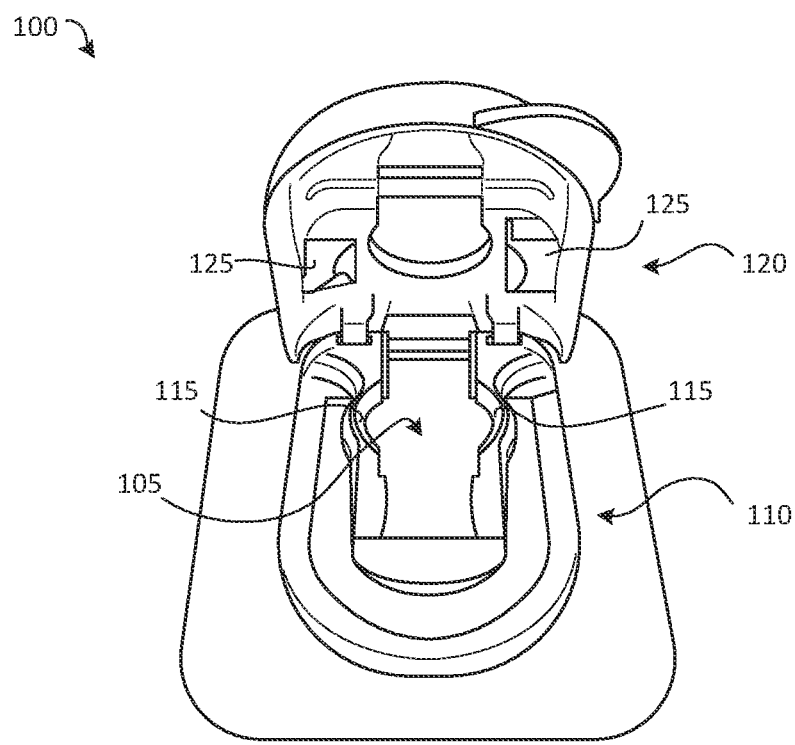

In various embodiments, and with reference to FIGS. 5A, 5B, and 5C, the lid 220 of the securement assembly 200 defines a receptacle 221. The receptacle 221 may facilitate retention of the cap 63 of the access device in response to a feeding tube 70 being connected to the external port 61 of the access device. That is, the cap 63 may be removed from its blocking position in the external port 61 to make way for a feeding tube 70, or other similar lumen, catheter, or delivery device, to be coupled to the external port 61. In order to keep the cap 63 in a known and secured position, the cap 63 may be temporarily inserted in the receptacle 221 to be retained.

In various embodiments, and with renewed reference to implementations in which the base 110 comprises the central portion 114 (see FIGS. 6A and 6B), the opposing side arms 115 of the central portion 114 may define an aperture through which a tube/stem of the access device extends. These opposing side arms 115 may also comprise chamfered edges, or may otherwise be shaped to receive and support the external support (e.g., the hub) of the access device. In various embodiments, the side arms 115 of the central portion 114 are resiliently flexible to facilitate selective enhanced retention of the external port of the access device. Said differently, the side arms 115 of the central portion 114 may be compressed by a practitioner to deflect the side arms toward each other, thereby providing augmented support and stability to the external port of the access device when needed. For example, when attaching a feeding tube or other such device, it may be helpful for the access device to be further stabilized to avoid pushing it into the patient's anterior abdominal wall, which would be painful for the patient. In various embodiments, the lid 120 (e.g., an underside of the lid) of the securement assembly 100 comprises one or more engagement features configured to engage the side arms 115 of the central portion 114 to transfer a user applied compression force from the lid 120 to the side arms 115 of the central portion 114 to facilitate the selective enhanced retention of the external port of the access device.

Figure 7A:
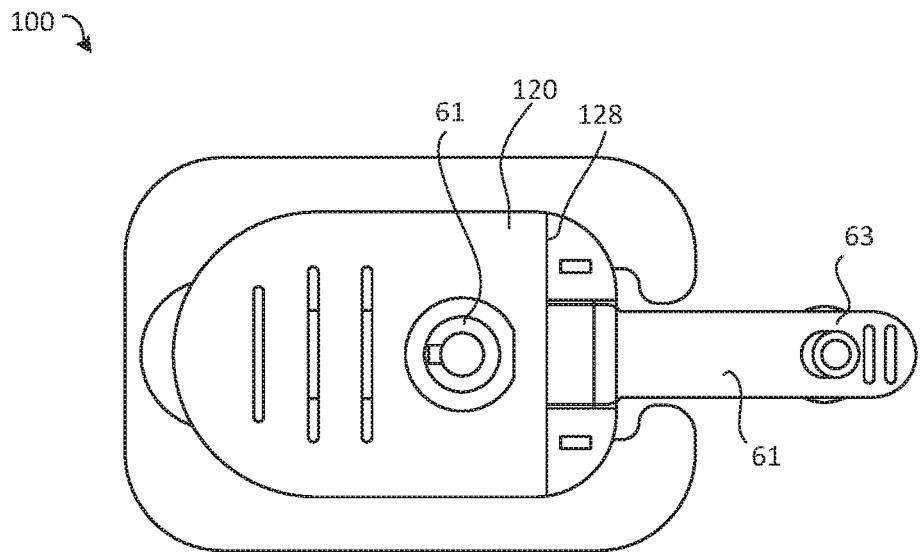
FIGS. 7A and 7B are top views of a deformable lid of a securement assembly for facilitating selective enhanced retention of an external port of an access device, in accordance with various embodiments.
Figure 7B:
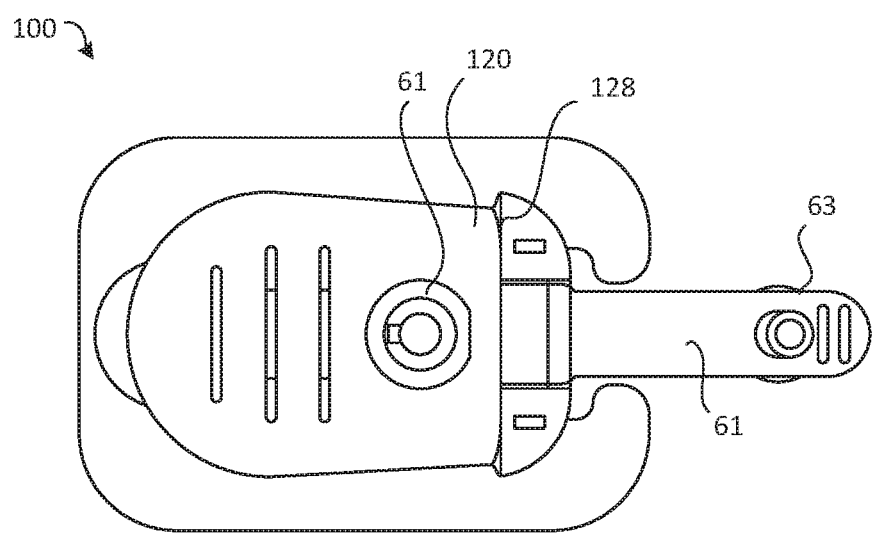

In various embodiments, and with reference to FIGS. 7A and 7B, at least a portion of the lid 120 is made from a resiliently deformable material, thus allowing the aforementioned compression of the lid 120 to provide the enhanced retention of the access device. In various embodiments, the lid 120 defines a slit 128 that accommodates the compression/deformation of the lid 120 in response to the user applied compression force.

As mentioned above, the lid 120 is generally configured to extend across the base 110 to serve as a protective barrier/shield to the base 110 and the supported access device. In various embodiments, and with momentary reference to FIG. 2, the securement assembly 100 may include a deformable lid cover 150 configured to be detachably coupled to the lid 120 to cover an upper and/our outer surface of the lid 120, thereby preventing articles or objects from becoming caught in the various exposed interfaces of the securement assembly 100.

Figure 8A:
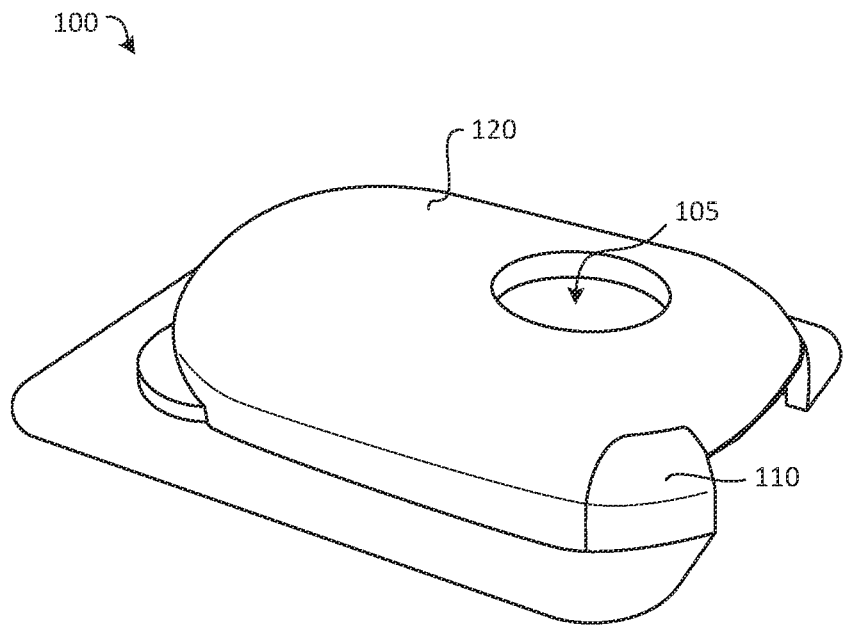
FIGS. 8A and 8B are views of substantially continuous outer surface of a securement assembly to prevent articles and objects from catching on any interfaces of the securement assembly, in accordance with various embodiments.
Figure 8B:
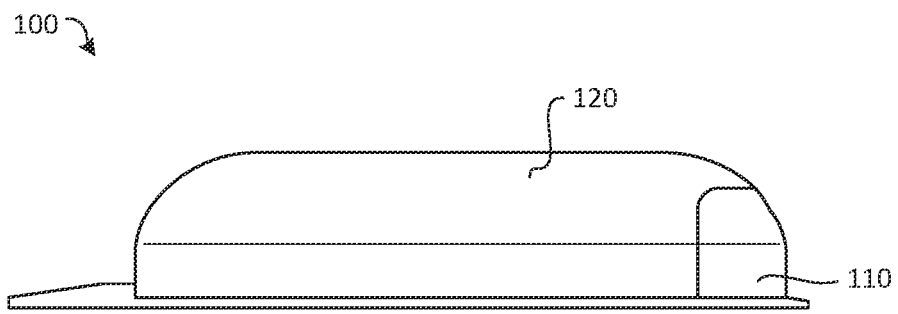
Figure 9A:
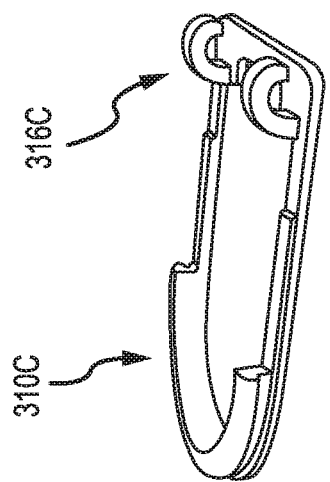
Figure 9B:
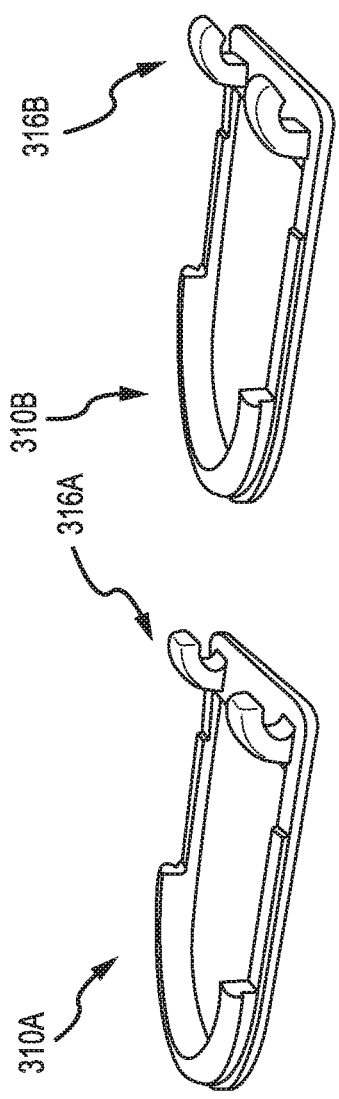
Figure 9C:
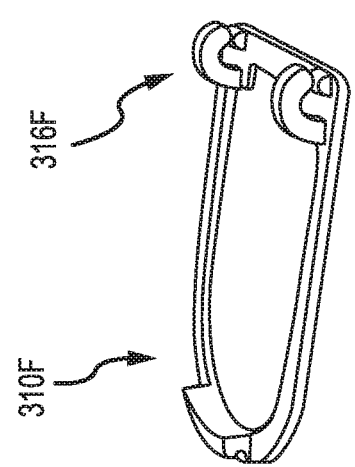
Figure 9D:
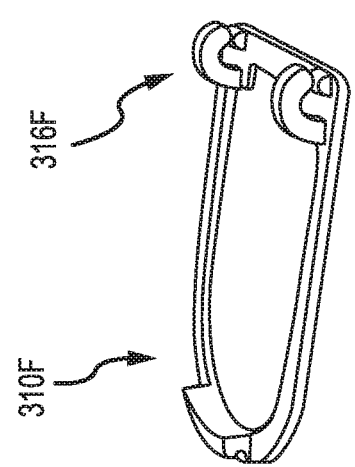
Figure 9E:
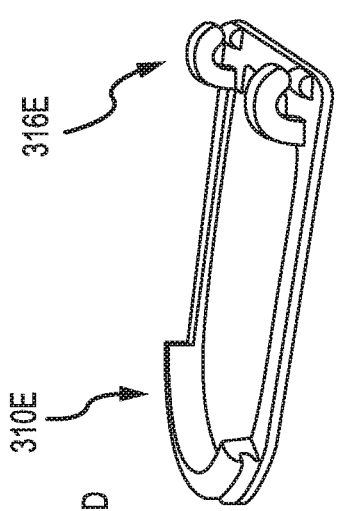
Figure 9F:
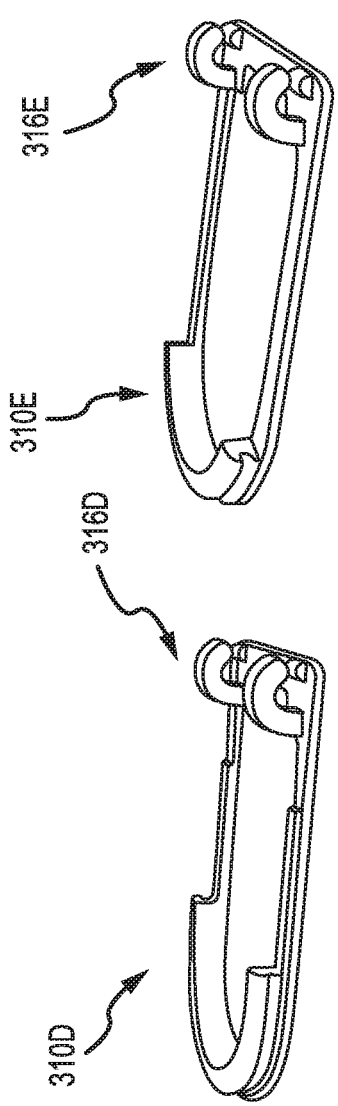

In various embodiments, and with reference to FIGS. 8A and 8B, to provide the aforementioned catch-prevention, the upper and/or outer surface of the securement assembly, defined by the lid 120 and also potentially defined by at least portion of the base 110, may be substantially smooth and continuous (e.g., may be free of abrupt corners or interfaces). Said differently, the outer/upper surface of the securement assembly may be designed to prevent articles and objects from catching on any interfaces of the securement assembly. For example, tangents of outer surfaces of the base and the lid adjacent junction interfaces between the base and the lid are substantially parallel, thus preventing articles from being snagged at the junction interfaces between the base and the lid.

In various embodiments, and with reference to FIGS. 9A, 9B, 9C, 9D, 9E, 9F, 9G, 9H, 10A, 10B, 11A, 11B, 12A, 12B, 13A, 13B, 13C, 13D, 14A, and 14B, various configurations of a hinged connection between the base and the lid of the securement assembly are provided. As mentioned above, the pivoting coupling between the base and the lid of the securement assembly may provide various benefits, such as easy access to replace the absorbent member. The various hinged connection structures described below with reference to these figures are specifically configured to enable selective detachment of the lid from the base. That is, as mentioned above, it may be advantageous for the lid to be detached from the base and reused with a replacement base.

However, in order for the securement assembly 100 to be useable for children, the selective, detachable, hinged connection should be configured to prevent children from being able to disconnect the parts (choking hazard) once installed on the skin but should be configured to allow practitioners to decouple the components during a base replacement procedure. Accordingly, the securement assembly may comprise a child proof state in which the lid is inhibited from being decoupled from the base by a child/infant. Whether the securement assembly is in the safe, child proof state or whether it is in the detachable state may be dependent upon the angled orientation of the lid relative to the base. Said differently, in response to the lid being in a first angular orientation relative to the base, the lid is prevented from being decoupled from the base (i.e., is in a "child proof state"), wherein in response to the lid being in a second angular orientation relative to the base the lid is detachable from the base. In various embodiments, the lid is configured to be pivotably coupled to the base before the base is adhered to a skin surface. In other words, the skin surface of the patient may limit the rotational movement of the lid (relative to the base) such that the lid is not removable until the base is detached from the skin. In various embodiments, as described in greater detail with reference to FIG. 16, direct engagement/contact between the lid and the base may limit the range of pivoting motion of the lid.

In various embodiments, and with reference to FIGS. 9A, 9B, 9C, 9D, 9E, 9F, 9G, 9H, the base 310A, 310B, 310C, 310D, 310E, 310F (collectively 310) of the securement assembly 300 may have one or more curved prongs 316A, 316B, 316C, 316D, 316E, 316F (collectively 316) configured to receive one or more rods 326, respectively, disposed at the end of the lid 320 of the securement assembly. For example, a rear of the base 310 may have a pair of curved prongs 316, and these curved prongs 316 may be configured to receive corresponding cylindrical rods/shafts disposed at an end of the lid 320 to form the hinged connection. The rods/shafts may be a section of a U-shaped extension extending from an end of the lid 320. The curved prongs 316 may define an entrance interface through which the corresponding rods are configured to be inserted (e.g., snap fit). This entrance interface may be configured to face outward and substantially downward, thus only enabling insertion and extraction of the rods 326 of the lid 320 from a certain position. This outward and/or downward orientation of the entrance interface of the curved prongs may be configured such that the lid 320 is only able to be coupled to and decoupled from the base 310 when the base 310 is not adhered to the skin of the patient (i.e., providing the securement assembly in the child proof state in response to the base being coupled to the skin of the patient).

Figure 10A:
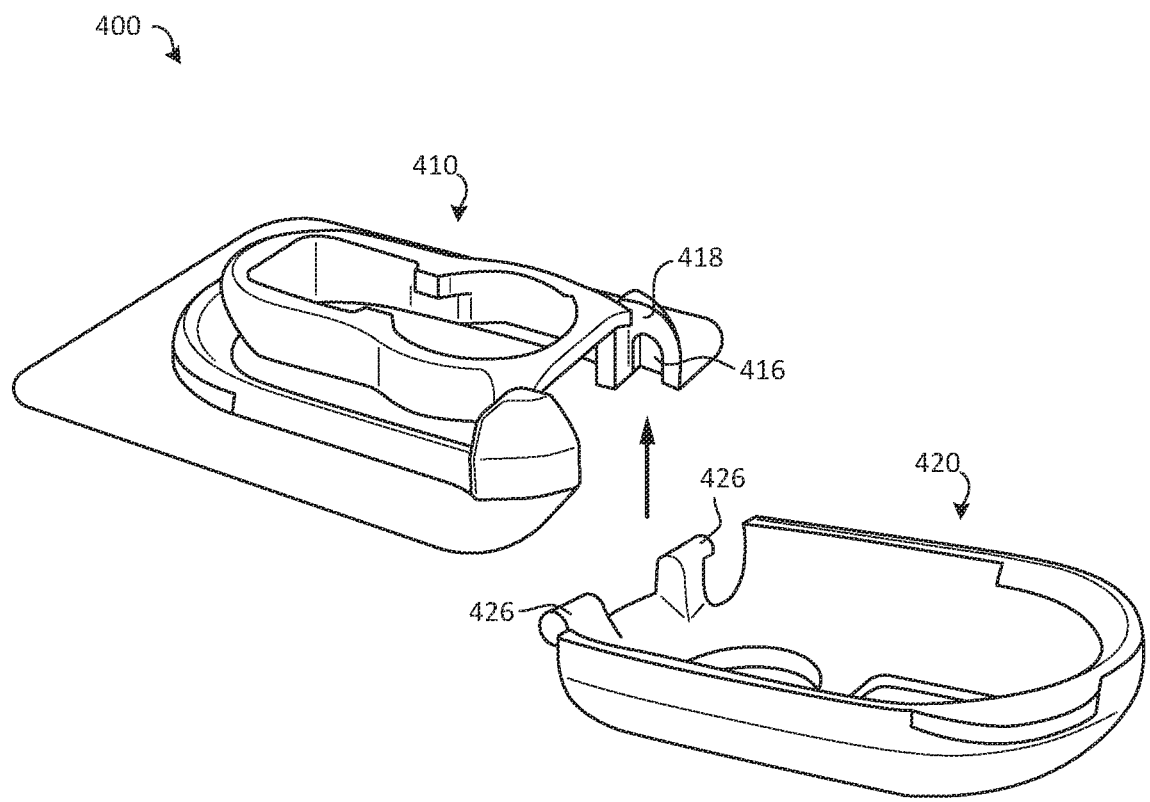
FIGS. 10A and 10B are perspective views of another hinged connection configuration between a base and a lid of a securement assembly, in accordance with various embodiments.
Figure 10B:
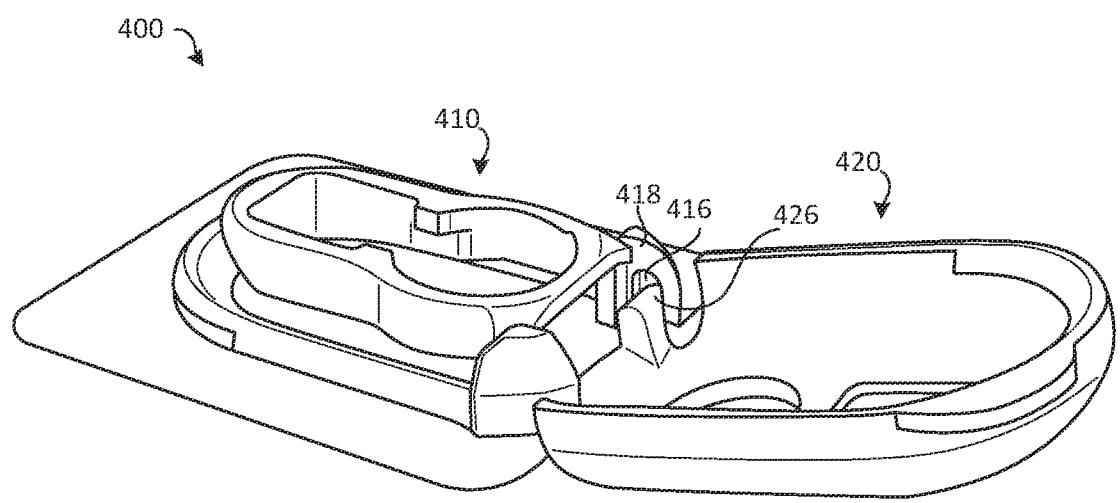

In various embodiments, and with reference to FIGS. 10A and 10B, another configuration of a hinged connection between the base 410 and the lid 420 of the securement assembly 400 is provided. In various embodiments, lateral sides of a rear 418 of the base 410 define opposing channels 416 that face inward. The lid 420 may comprise laterally extending cylindrical protrusions 426. A hinge axis (e.g., a hinged connection) may be formed and defined between the base 410 and the lid 420 in response to the opposing channels 416 receiving the laterally extending cylindrical protrusions 426 of the lid 420. In various embodiments, each channel of the opposing channels 416 has an open lower end and a closed upper end.

Figure 11A:
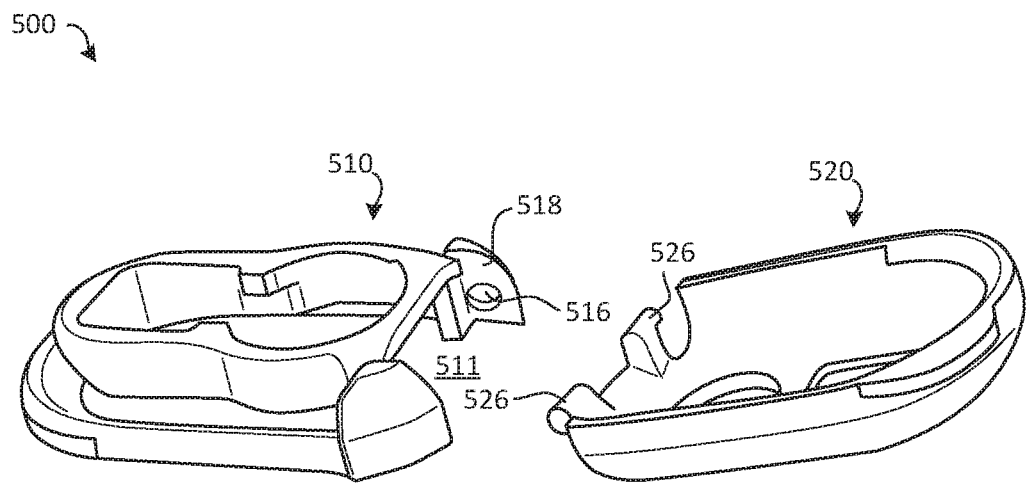
FIGS. 11A and 11B are perspective views of another hinged connection configuration between a base and a lid of a securement assembly, in accordance with various embodiments.
Figure 11B:
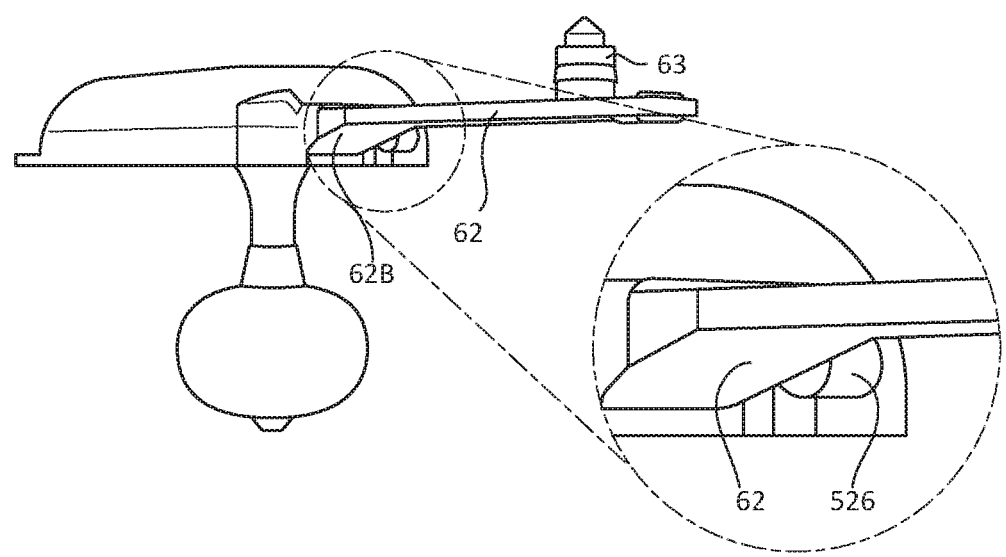

In various embodiments, and with reference to FIGS. 11A and 11B, another configuration of a hinged connection between the base 510 and the lid 520 of the securement assembly 500 is provided. In various embodiments, lateral sides of the rear 518 of the base 510 define opposing dimples/recesses 516 that face inward. The lid 520 may comprise laterally extending cylindrical protrusions 526. A hinge axis (e.g., a hinged connection) may be formed and defined between the base 510 and the lid 520 in response to the opposing dimples 516 receiving the laterally extending cylindrical protrusions 526 of the lid 520. In various embodiments, engagement between the cylindrical protrusions 526 and the corresponding dimples 516 is a snap-fit that still enables relative rotation.

In various embodiments, and with continued reference to FIGS. 11A and 11B, the base 510 of the securement assembly 500, at a rear of the base 510, defines a gap 511. In various embodiments, this gap 511 is a window, opening, or aperture defined in the border rim of the base 510, and the connecting strap 62 for the cap 63 of the access device is configured to extend through this gap 511. Said differently, instead of the lid having an opening or aperture through which the connecting strap 62 for the cap 63 extends, this connecting strap 62 may be configured to pass through the gap 511 defined by the base 510 and wrap up and around the rear and top surface of the lid to plug/engage the external port of the access device. Said differently, the lid has an aperture through which the cap 63 of the access device extends, but the lid does not have an aperture through which the connecting strap 62 extends, according to various embodiments. In such a configuration, with the lid being coupled to the base at a hinge axis, the gap defined by the border rim of the base is configured such that the connecting strap 62 either intersects the hinge axis or extends below the hinge axis. With the connecting strap 62 so positioned, the connecting strap 62 may inhibit unwanted/premature detachment of the lid from the base. For example, the strap 62 may extend between the separate opposing cylindrical protrusions of FIGS. 10A and 11A, thereby inhibiting compressive deformation of this portion of the lid and thereby reducing the likelihood of these protrusions 426, 526, falling out of engagement with the corresponding channel 416 or dimple 516. Similarly, with the strap 62 extending below the hinge axis, as described and shown in greater detail below, the hinge axis is blocked from moving downward by the strap 62, thus helping to maintain the hinged connection between the lid and the base.

Figure 12A:
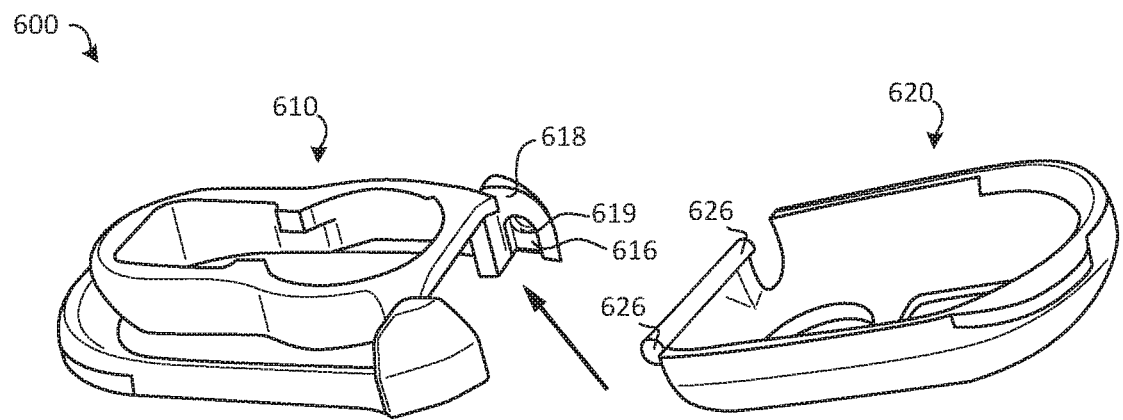
FIGS. 12A and 12B are perspective views of another hinged connection configuration between a base and a lid of a securement assembly, in accordance with various embodiments.
Figure 12B:
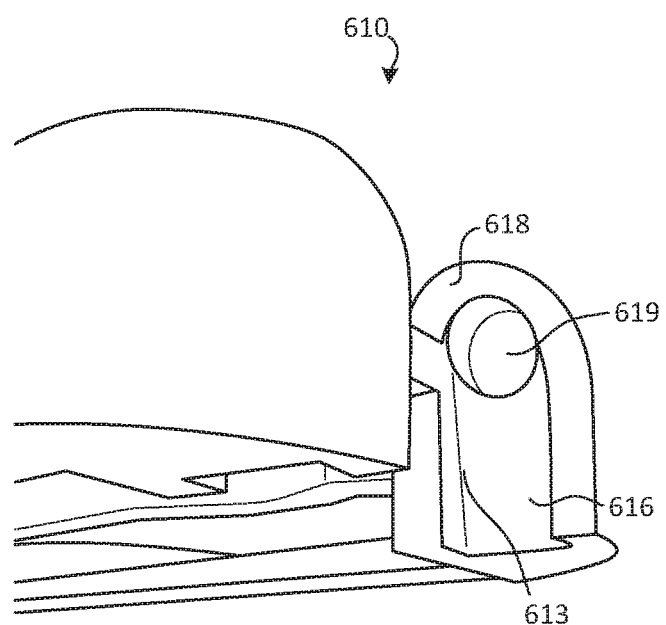

In various embodiments, and with reference to FIGS. 12A and 12B, another configuration of a hinged connection between the base 610 and the lid 620 of the securement assembly 600 is provided. In various embodiments, lateral sides of the rear 618 of the base 610 define opposing channels 616 and opposing dimples/recesses 619 formed adjacent the closed end of said channels 616. The lid 620 may comprise laterally extending cylindrical protrusions 626, and a hinge axis (e.g., a hinged connection) may be formed and defined between the base 610 and the lid 620 in response to the opposing channels 616 and dimples 619 receiving the laterally extending cylindrical protrusions 626 of the lid 620.

In various embodiments, engagement between the cylindrical protrusions 626 and the corresponding dimples 619 is a snap-fit that still enables relative rotation. In various embodiments, the laterally extending cylindrical protrusions are opposing ends of a continuous section of material of the lid 620 that extends between the opposing ends. In various embodiments, the lid 620 includes a continuous rod/shaft extending across the rear of the lid 620. In various embodiments, at least one of the channels of the opposing channels 616 may have a tapering wall 613 that converges toward the other opposing channel from the open lower end to the closed upper end. This tapering wall 613 may facilitate insertion of the opposing cylindrical protrusions into the corresponding dimples 619.

In various embodiments, and with reference to FIGS. 13A, 13B, 13C, and 13D, another configuration of a hinged connection between the base 710 and the lid 720 of the securement assembly 700 is provided. In various embodiments, lateral sides of the rear 718 of the base 710 define opposing channels 716. The opposing channels 716 also define tracks 717 configured to guide and receive a flanged protrusion of the lid. That is, the lid 720 may have laterally extending cylindrical protrusions 726 that have a flange 727 feature, and the hinge axis (e.g., a hinged connection) may be formed and defined between the base 710 and the lid 720 in response to the opposing channels 716 and tracks 717 receiving the laterally extending cylindrical protrusions 726 and flanges 727 of the lid 720. In various embodiments, the opposing channels 716 and corresponding tracks 717 may have a rounded introductory corner configured to facilitate initial engagement of the protrusions within the channels/tracks.

Figure 14A:
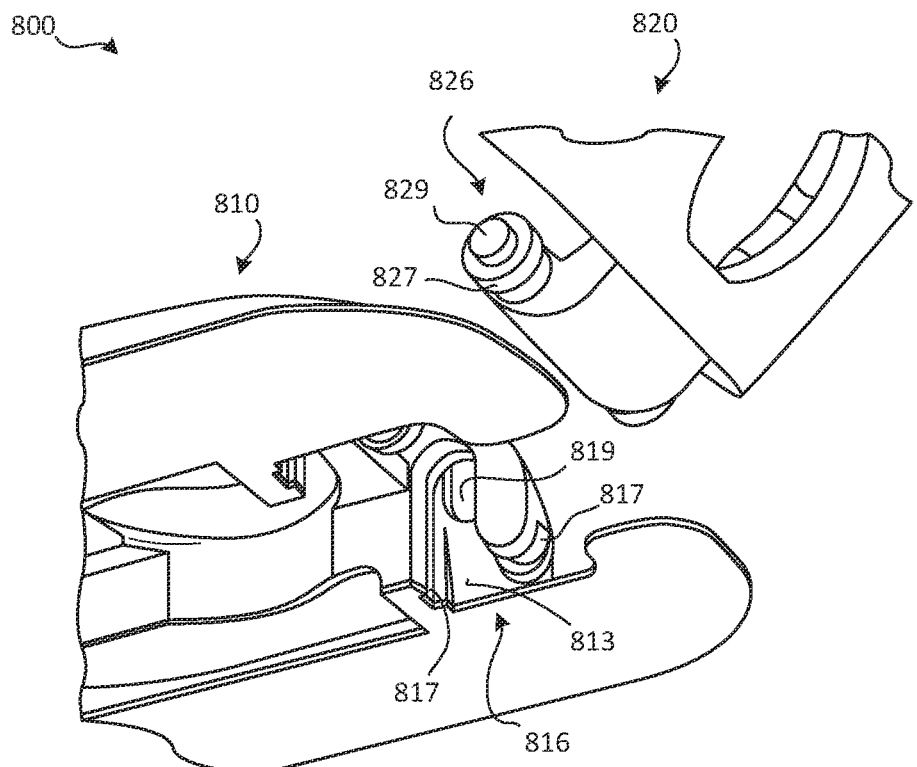
FIGS. 14A and 14B are views of yet another hinged connection configuration between a base and a lid of a securement assembly, in accordance with various embodiments.
Figure 14B:
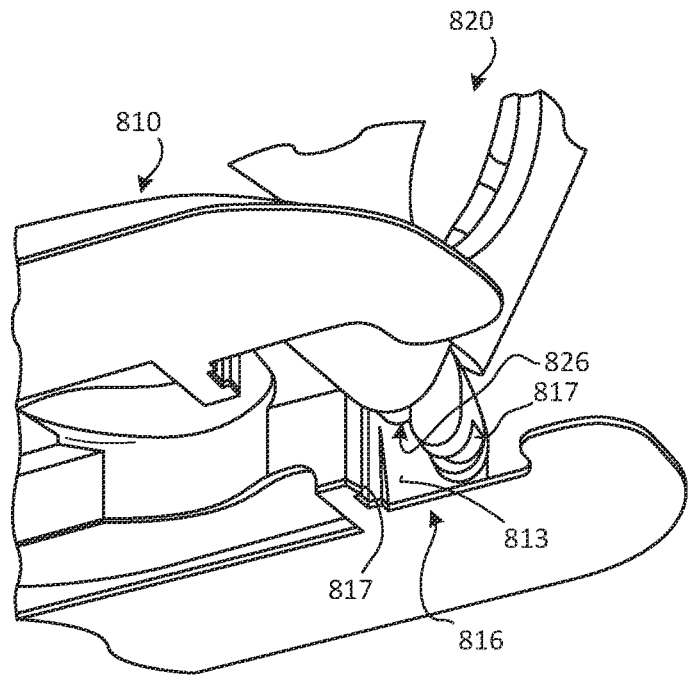

In various embodiments, and with reference to FIGS. 14A and 14B, another configuration of a hinged connection between the base 810 and the lid 820 of the securement assembly 800 is provided. In various embodiments, lateral sides of the rear of the base 810 define opposing channels 816, tracks 817, and dimples 819. The hinged connection between the base 810 and the lid 820 may be formed in response to the opposing channels 816 and corresponding tracks 817 receiving the laterally extending cylindrical protrusions 826 and flanges 827 of the lid 820 until the protrusions 826 are guided and received into the corresponding dimples 819 of the base 810. As mentioned above, the opposing channels may include one or more tapering walls 813 that converge toward the other opposing channel from the open lower end to the closed upper end. This tapering wall 813 may facilitate insertion of the opposing cylindrical protrusions into the corresponding dimples 819.

Figure 15A:
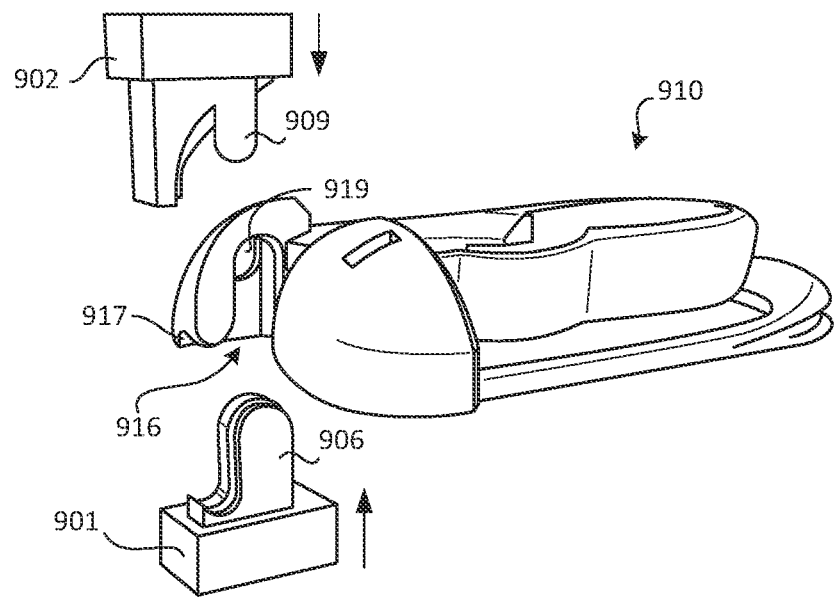
FIGS. 15A and 15B show details pertaining to a step of a method for manufacturing a securement assembly, in accordance with various embodiments.
Figure 15B:
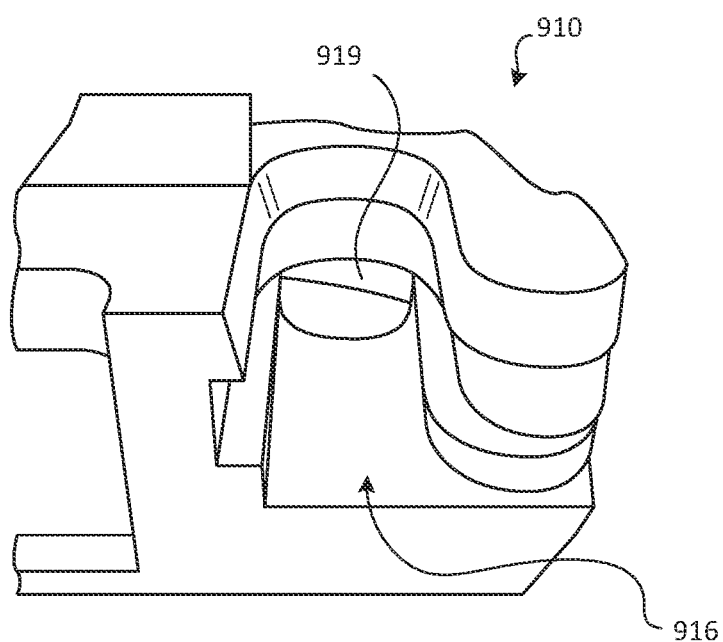

The base and/or the lid of the securement assembly may be formed using an additive manufacturing process, an injection molding process, a polymer casting process, and/or utilizing various other methods, such as stamping and computer numerical control machining, water-jetting, and laser cutting. In various embodiments, and with reference to FIG. 15A, two linear pull molds 901, 902 for an injection molding process are shown. The pull molds are configured to be utilized to form the channel 916, track 917, and open dimple 919 of the base 910 of the securement assembly. In various embodiments, the first pull mold 901 has features 906 configured to form the channel 916 and tracks 917 and the second pull mold 902 has features 909 that form the open dimple 919. The open dimple 919, instead of having a closed end, has a removed ceiling formed by the second pull mold 902. The open dimple 919 still provides the same level of retention as dimple 819, for example, because the ends of the cylindrical protrusions are still retained by the ceiling of the notched inner cavity and the floor of the dimple 919.

Figure 16:
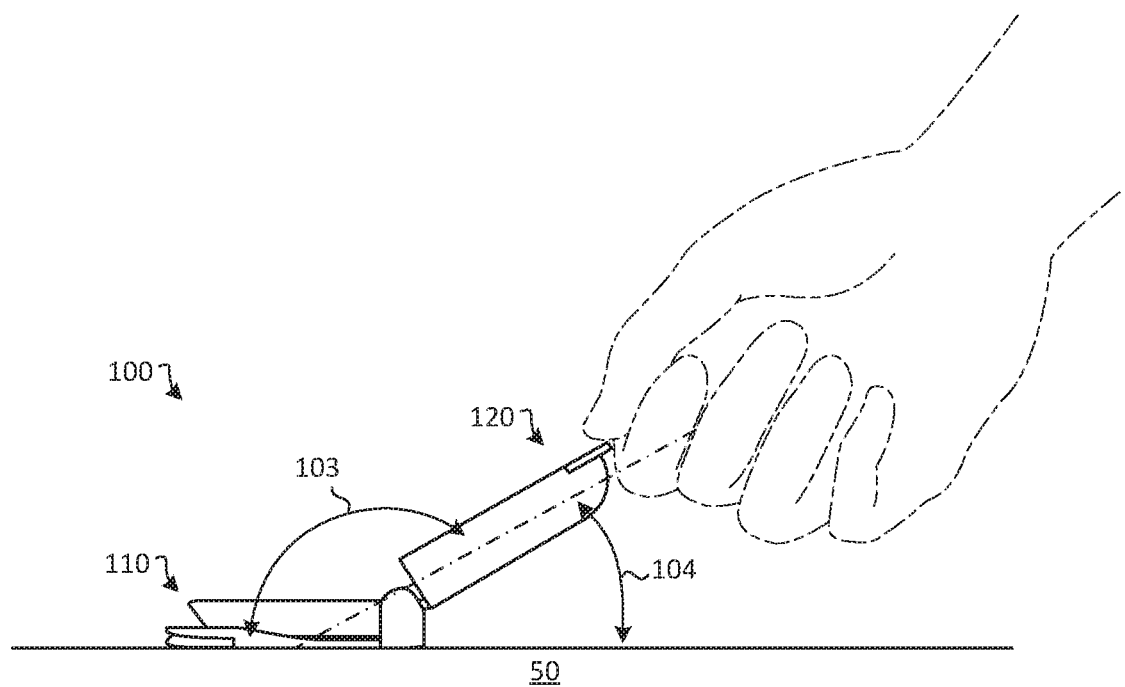
FIG. 16 is a side view of a securement assembly showing an angle between a base and a lid (and a corresponding angle between the lid and a skin surface of a patient), in accordance with various embodiments.

In various embodiments, and with reference to FIG. 16, a first angle 103 between the base 110 and the lid 120 and a corresponding second angle 104 between the lid 120 and the skin surface 50 of the patient is shown. As mentioned above, detachment of the lid 120 from the base 110 may be prevented because the lid 120 is blocked by the skin surface 50 from rotating far enough to allow detachment of the lid. In various embodiments, instead of relying on the skin surface 50 as the blocking element that limits the pivoting motion of the lid 120, engagement of the rear portion of the border edge of the lid 120 with the rear of the base 110 creates the blocking contact to limit the pivoting motion, thus maintaining the securement assembly in the child proof state.

Figure 17:
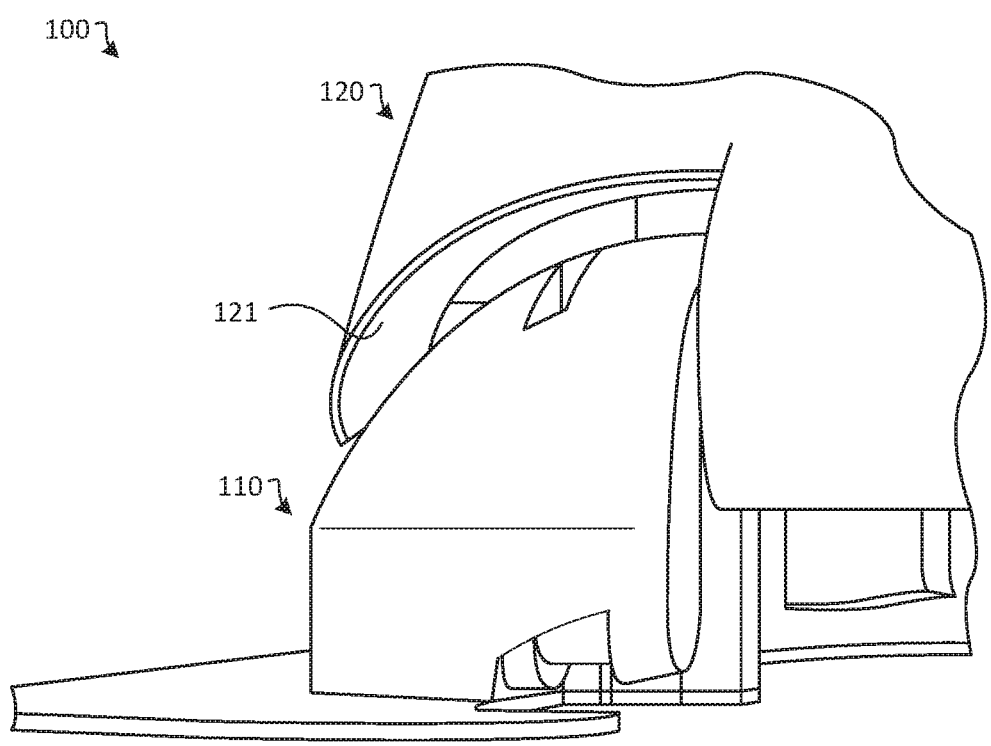
FIG. 17 is a perspective view of a rear of a securement assembly showing a chamfered edge of a lid of the securement assembly, in accordance with various embodiments.

In various embodiments, the configuration of the lid 120 and the base 110 is such that the second angle 104 is greater than 30 degrees. In such a configuration, the practitioner may grasp the lid 120 during installation of the securement assembly 100 and may utilize the lid 120 has a handle to manipulate and position the base 110 against the skin surface 50 of the patient. With the second angle not being less than 30 degrees, the practitioner's grasping hand does not engage the skin surface, thus allowing the practitioner to controllably articulate the position of the base 110 via the lid 120. In various embodiments, and with reference to FIG. 17, a rear border edge 121 of the lid 120 is chamfered to provide adequate clearance between the lid 120 and the rear of the base 110 during the pivoting motion. Said differently, at least a rear portion of a border edge 121 of the lid 120 may comprise a chamfer. This chamfered rear edge 121 allows the lid 120 to have a contact point with the base 110 that resulted in a desirable second angle 104 (as described above) while still providing sufficient clearance as the lid 120 pivots back around the base 110 to reduce the first angle 103 until the lid is coupled in the closed/connected position at the forward portion of the assembly.

Figure 18:
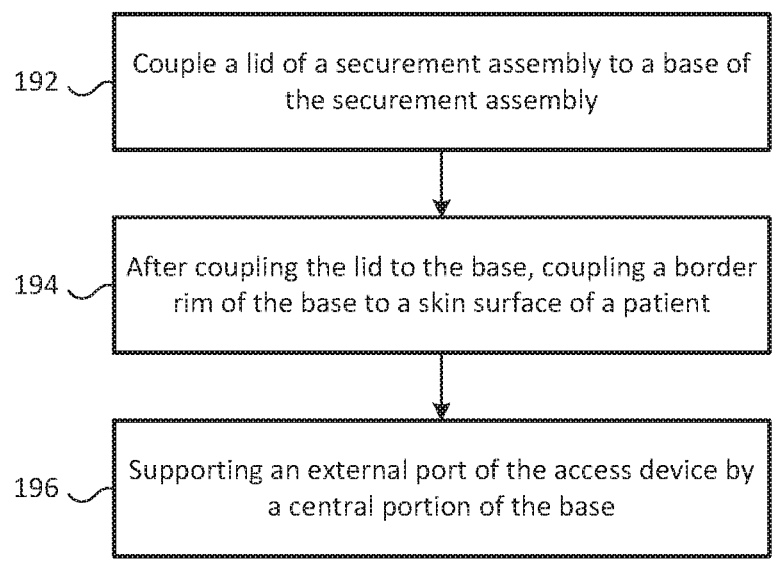
FIG. 18 is a schematic block diagram of a method of installing a securement assembly for an access device, in accordance with various embodiments.

In various embodiments, and with reference to FIG. 18, a method 190 of installing a securement assembly for an access device is provided. The method 190 may include coupling a lid of the securement assembly to a base of the securement assembly at step 192. After performing step 192, the method 190 may further include attaching a border rim of the base to a skin surface of a patient about a stoma of the patient (i.e., adhering the border rim to the skin surface using an adhering layer) at step 194. Still further, the method 190 may include supporting an external port of the access device by a central portion of the base at step 196. These method steps, as well as additional method steps, may be described above with reference to the preceding figures.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Also, any reference to attached, fixed, connected, coupled or the like may include permanent (e.g., integral), removable, temporary, partial, full, and/or any other possible attachment option. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A securement assembly for an enteral access device or vesical access device ("access device"), the securement assembly comprising:
    a base configured to support an external port of the access device, wherein the base comprises a border rim and a central portion, wherein the border rim is configured to engage a skin surface of a patient around a stoma and the central portion is configured to engage the external port of the access device, wherein the central portion comprises opposing side arms defining an aperture through which a tube of the access device extends, wherein the side arms of the central portion are resiliently flexible to facilitate selective enhanced retention of the external port of the access device, wherein the central portion is a cantilevered extension from a rear of the base;
    an absorbent member configured to be slid under the cantilevered extension and over the border rim into engagement with the skin surface around the stoma in an annular space defined between the border rim and the tube of the access device; and
    a lid pivotably coupled to the base.

2. A securement assembly for an enteral access device or vesical access device ("access device"), the securement assembly comprising:
    a base configured to support an external port of the access device, wherein the base comprises a border rim and a central portion, wherein the border rim is configured to engage a skin surface of a patient around a stoma and the central portion is configured to engage the external port of the access device, wherein the central portion comprises opposing side arms defining an aperture through which a tube of the access device extends, wherein the side arms of the central portion are resiliently flexible to facilitate selective enhanced retention of the external port of the access device, wherein the central portion is a cantilevered extension from a rear of the base;
    an absorbent member comprising opposing wings configured to extend beyond lateral sides of the base and configured to be slid under the cantilevered extension and over the border rim into engagement with the skin surface around the stoma in an annular space defined between the border rim and the tube of the access device, and the absorbent member defining a central aperture and a slit, wherein the tube of the access device extends through the central aperture; and a lid pivotably coupled to the base;

wherein at least one of the border rim and a border edge of the lid at the lateral sides of the base defines a notch to accommodate the opposing wings of the absorbent member.

3. The securement assembly of claim 2, wherein an underside of the lid comprises engagement features configured to engage the side arms of the central portion to transfer a user applied compression force from the lid to the central portion to facilitate the selective enhanced retention of the external port of the access device.

4. The securement assembly of claim 3, wherein the lid defines slits to facilitate deformation of the lid in response to the user applied compression force.

5. The securement assembly of claim 2, wherein the border rim at a rear of the base defines a gap through which a connecting strap of a cap of the access device is configured to extend.

6. The securement assembly of claim 5, wherein the lid is pivotably coupled to the base at a hinge axis, wherein the gap defined by the border rim of the base is configured such that the connecting strap of the access device either intersects the hinge axis or extends below the hinge axis.

7. The securement assembly of claim 2, wherein the lid is selectively detachably coupled to the base, wherein the lid is in a child proof state in response to the lid being in a first angular orientation relative to the base, wherein in the child proof state the lid is prevented from being decoupled from the base, wherein in response to the lid being in a second angular orientation relative to the base the lid is detachable from the base.

8. The securement assembly of claim 7, wherein the lid is configured to be coupled to the base before the base is adhered to a skin surface of a patient such that the securement assembly is in the child proof state in response to the lid being coupled to the base and the base being adhered to the skin surface.

9. The securement assembly of claim 7, wherein a rear of the base comprises a curved prong and the lid comprises a rod, wherein a hinge axis is formed between the base and the lid in response to the curved prong receiving the rod.

10. The securement assembly of claim 7, wherein lateral sides of a rear of the base define opposing channels that face inward, wherein the lid comprises laterally extending cylindrical protrusions, wherein a hinge axis is formed between the base and the lid in response to the opposing channels receiving the laterally extending cylindrical protrusions.

11. The securement assembly of claim 10, wherein each channel of the opposing channels has an open lower end and a closed upper end.

12. The securement assembly of claim 11, wherein the closed upper end of each channel defines a dimple configured to receive an end of a respective cylindrical protrusion of the laterally extending cylindrical protrusions.

13. The securement assembly of claim 11, wherein the opposing channels comprise tapering walls that converge toward each other from the open lower end to the closed upper end.

14. The securement assembly of claim 10, wherein the laterally extending cylindrical protrusions are opposing ends of a continuous section of material of the lid that extends between the opposing ends.

15. The securement assembly of claim 10, wherein the opposing channels define tracks and the laterally extending cylindrical protrusions comprise flange portions configured to be respectively received within the tracks.

16. The securement assembly of claim 15, wherein the tracks comprise rounded entry corners to facilitate insertion of the flange portions within the tracks.

17. The securement assembly of claim 7, wherein at least a rear portion of a border edge of the lid comprises a chamfer.

18. The securement assembly of claim 17, wherein engagement of the rear portion of the border edge of the lid with a rear of the base facilitates maintaining the securement assembly in the child proof state.

19. The securement assembly of claim 2, wherein the lid defines a receptacle for detachably retaining a cap of the access device.

20. The securement assembly of claim 2, further comprising a deformable lid cover configured to be detachably coupled to the lid to cover an upper surface of the lid.

21. The securement assembly of claim 2, wherein tangents of outer surfaces of the base and the lid adjacent junction interfaces between the base and the lid are substantially parallel, thus preventing articles from being snagged at the junction interfaces between the base and the lid.

22. A securement assembly for an enteral access device or vesical access device ("access device"), the securement assembly comprising:

a base comprising a border rim and a central portion, wherein the border rim is configured to engage a skin surface of a patient around a stoma and the central portion is configured to engage an external port of the access device, wherein the central portion comprises opposing side arms defining an aperture through which a tube of the access device extends, wherein the side arms of the central portion are resiliently flexible to facilitate selective enhanced retention of the external port of the access device, wherein the central portion is a cantilevered extension from a rear of the base;

an absorbent member configured to be slid under the cantilevered extension and over the border rim into engagement with the skin surface around the stoma in an annular space defined between the border rim and the tube of the access device; and a lid selectively detachably and pivotably coupled to the base.

23. A method of installing a securement assembly for an enteral access device or vesical access device ("access device"), the method comprising:

coupling a lid of the securement assembly to a base of the securement assembly, wherein the base comprises a border rim and a central portion, wherein the border rim is configured to engage a skin surface of a patient around a stoma and the central portion is configured to engage the external port of the access device, wherein the central portion comprises opposing side arms defining an aperture through which a tube of the access device extends, wherein the side arms of the central portion are resiliently flexible to facilitate selective enhanced retention of the external port of the access device, wherein the central portion is a cantilevered extension from a rear of the base;

after coupling the lid of the securement assembly to the base of the securement assembly, adhering the border rim of the base to the skin surface of the patient about the stoma of the patient;

sliding an absorbent member under the cantilevered extension and over the border rim into engagement with the skin surface around the stoma in an annular space defined between the border rim and the tube of the access device; and supporting an external port of the access device by the central portion of the base.

\* \* \* \* \*